US008563008B2

(12) United States Patent
Deloron et al.

(10) Patent No.: US 8,563,008 B2
(45) Date of Patent: Oct. 22, 2013

(54) POLYNUCLEOTIDES AND POLYPEPTIDES INVOLVED IN GESTATIONAL MALARIA, AND BIOLOGICAL APPLICATIONS

(75) Inventors: Philippe Lucien Deloron, Paris (FR); Nicaise George Tuikue Ndam, Paris (FR); Gwladys Irénée Bertin, Neuilly Plaisance (FR); Peter David, Paris (FR); Emmanuel Bischoff, Boulogne-Billancourt (FR); Caroline Stéphanie Proux, Montigny le Bretonneux (FR); Jean-Yves Coppee, Paris (FR); Ali Salanti, Broenshoj (DK); Thomas Lavstsen, Hoersholm (DK)

(73) Assignees: Institut de Recherche pour le Development (IRD), Marseille Cedex (FR); Institut Pasteur, Paris (FR)

( * ) Notice: Subject to any disclaimer, the term of this patent is extended or adjusted under 35 U.S.C. 154(b) by 201 days.

(21) Appl. No.: 12/450,874

(22) PCT Filed: Apr. 17, 2008

(86) PCT No.: PCT/IB2008/051482
§ 371 (c)(1),
(2), (4) Date: Oct. 16, 2009

(87) PCT Pub. No.: WO2008/126065
PCT Pub. Date: Oct. 23, 2008

(65) Prior Publication Data
US 2010/0255018 A1  Oct. 7, 2010

(30) Foreign Application Priority Data
Apr. 17, 2007  (FR) ...................... 07 02772

(51) Int. Cl.
A61K 39/00 (2006.01)
A61K 39/38 (2006.01)
A61K 39/015 (2006.01)
A61K 38/00 (2006.01)
C07H 21/02 (2006.01)
C07K 14/00 (2006.01)
C07K 17/00 (2006.01)

(52) U.S. Cl.
USPC ................ 424/268.1; 424/265.1; 424/184.1; 424/185.1; 536/23.1; 530/300; 530/350

(58) Field of Classification Search
None
See application file for complete search history.

(56) References Cited

U.S. PATENT DOCUMENTS

2007/0036819 A1 * 2/2007 Fried et al. ................. 424/191.1

FOREIGN PATENT DOCUMENTS

WO  WO 2006/124712  11/2006

OTHER PUBLICATIONS

GenEmbl accession No. EU181220, Apr. 4 2008.*
Pinto et al. (2011) Differential Induction of Functional IgG Using the *Plasmodium falciparum* Placental Malaria Vaccine Candidate VAR2CSA. PLoS One 6(3): e17942. doi:10.1371/journal.pone.0017942.*
Houghten et al. New Approaches to Immunization, Vaccines 86, Cold Spring Harbor Laboratory, p. 21-25 and p. 74 1986.*
Abbas et al. Cellular and Molecular Immunology 2000 Chapter 15 p. 360-362.*
Ellis, R.W. (Chapter 29 of "Vaccines" [Plotkin, S.A. et al. (eds) published by W. B. Saunders company (Philadelphia) in 1988.*
Oplinger et al NIH record vol. LVII No. 9.*
Tongren et al. Trends in Parasitology vol. 20 Dec. 2004 p. 604-610.*
Struik and Riley, Immunological Reviews 2004, vol. 201:268-290.*
Crompton et al. The Journal of Clinical Investigation vol. 120 No. 12 p. 4168-4178, 2010.*
Herbet et al. The Dictionary of Immunology, Academic Press, 1995: definition of "vaccine".*
International Search Report for PCT/IB2008/051482, mailed Nov. 7, 2008.
Database Abstract, "Putative uncharacterized protein PFI1785w", Accession No. Q8I2F1, 1 page, (Mar. 1, 2003).
Fried, Michal et al., "The distinct proteome of placental malaria parasites", Molecular and Biochemical Parasitology Sep, vol. 155, No. 1, pp. 57-65, (Sep. 2007).
Frances, Susan E. et al., "Six genes are preferentially transcribed by the circulating and sequestered forms of *Plasmodium falciparum* parasites that infect pregnant women.", Infection and Immunity, vol. 75, No. 10, pp. 4838-4850, (Oct. 2007).
Tuikue Ndam, N. et al., "*Plasmodium falciparum* transcriptome and analysis reveals pregnancy malaria associated gene expression.", PLOS ONE, vol. 3, No. 3, pp. 1-9, (Mar. 26, 2008).
Bigey et al, "The NTS-DBL2X Region of VAR2CSA Induces Cross-Reactive Antibodies That Inhibit Adhesion of Several *Plasmodium falciparum* Isolates to Chondroitin Sulfate A", The Journal of Infectious Diseases 2011:204 (Oct. 1), pp. 1125-1133.

* cited by examiner

*Primary Examiner* — Oluwatosin Ogunbiyi
(74) *Attorney, Agent, or Firm* — Nixon & Vanderhye P.C.

(57) ABSTRACT

The disclosure provides novel antigens involved in gestational malaria, and more particularly to polynucleotide and polypeptide sequences, conjugates, cloning vectors including the sequences for the preparation of immunogenic compositions and vaccines, antibodies, and to their for treating gestational malaria. Diagnostic methods and kits are described.

10 Claims, 12 Drawing Sheets

Figure 7A

Figure 1:
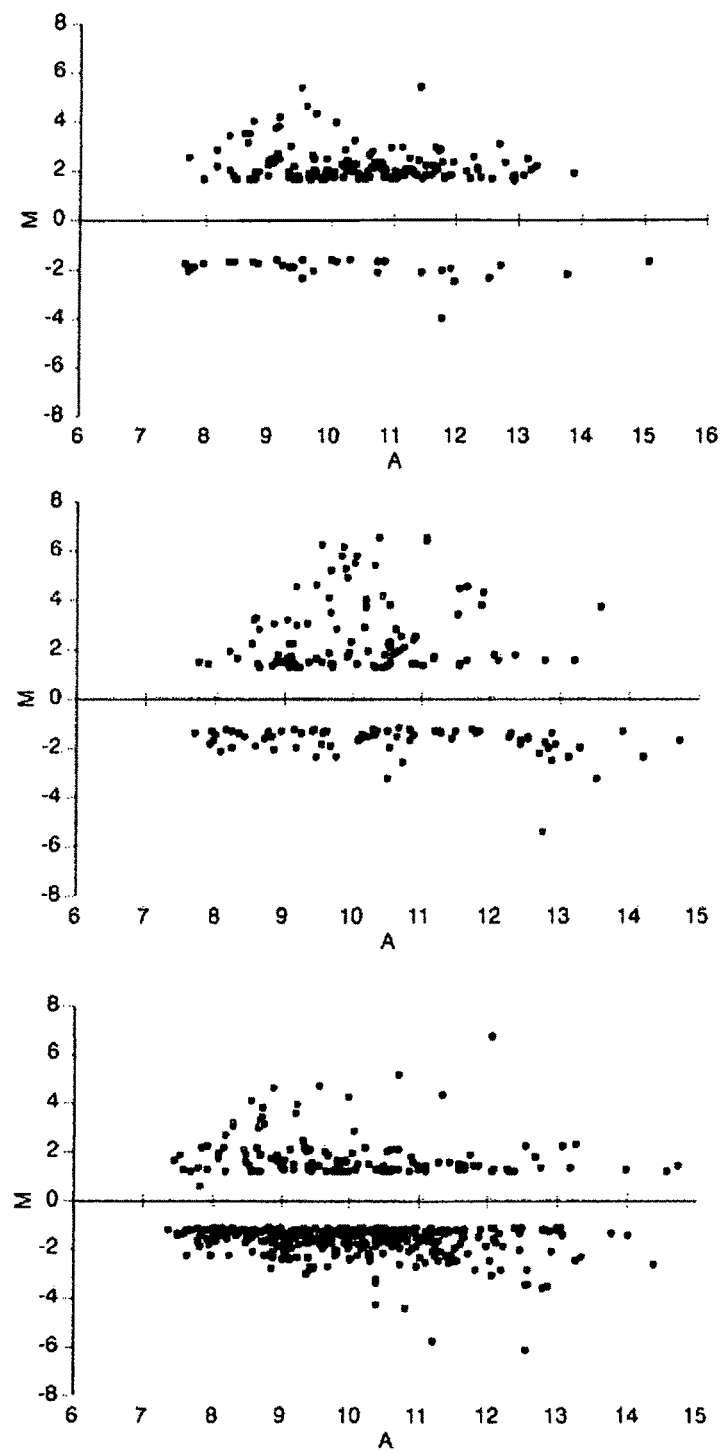

```
              1                                                    50
         21   ATGTGGTTTT GTAATAAATT TAATGATAAT ACAACTAAAG GGTTACTGGA
         22   ATGTGGTTTT GTAATAAATT TAATGATAAT ACAACTAAAG GGTTACTGGA
         23   ATGTGGTTTT GTAATAAATT TAATGATAAT ACAACTAAAG GGTTACTGGA
         24   ATGTGGTTTT GTAATAAATT TAATGATAAT ACAACTAAAG GGTTACTGGA
         25   ATGTGGTTTT GTAATAAATT TAATGATAAT ACAACTAAAG GGTTACTGGA
         26   ATGTGGTTTT GTAATAAATT TAATGATAAT ACAACTAAAG GGTTACTGGA
  Consensus   ATGTGGTTTT GTAATAAATT TAATGATAAT ACAACTAAAG GGTTACTGGA 51                                                  100
         21   TTCTAATAAT GTACAATCAA AATATTGTAC CATATATTCT TTTGATGATG
         22   TTCTAATAAT GTACAATCAA AATATTGTAC CATATATTCT TTTGATGATG
         23   TTCTAATAAT GTACAATCAA AATATTGTAC CATATATTCT TTTGATGATG
         24   TTCTAATAAT GTACAATCAA AATATTGTAC CATATATTCT TTTGATGATG
         25   TTCTAATAAT GTACAATCAA AATATTGTAC CATATATTCT TTTGATGATG
         26   TTCTAATAAT GTACAATCAA AATATTGTAC CATATATTCT TTTGATGATG
  Consensus   TTCTAATAAT GTACAATCAA AATATTGTAC CATATATTCT TTTGATGATG 101                                                 150
         21   AAGAAAATAA TACGAAAAGA AAAAATCAGT TCGCATCTTT TAGTAAATTA
         22   AAGAAAATAA TACGAAAAGA AAAAATCAGT TCGCATCTTT TAGTAAATTA
         23   AAGAAAATAA TACGAAAAGA AAAAATCAGT TCGCATCTTT TAGTAAATTA
         24   AAGAAAATAA TACGAAAAGA AAAAATCAGT TCGCATCTTT TAGTAAATTA
         25   AAGAAAATAA TACGAAAAGA AAAAATCAGT TCGCATCTTT TAGTAAATTA
         26   AAGAAAATAA TACGAAAAGA AAAAATCAGT TCGCATCTTT TAGTAAATTA
  Consensus   AAGAAAATAA TACGAAAAGA AAAAATCAGT TCGCATCTTT TAGTAAATTA 151                                                 200
         21   TGTTTAAAGT TATGTATTCT TGGAATTATT GTAATAGTGG TATGTCAAAA
         22   TGTTTAAAGT TATGTATTCT TGGAATTATT GTAATAGTGG TATGTCAAAA
         23   TGTTTAAAGT TATGTATTCT TGGAATTATT GTAATAGTG. ..........
         24   TGTTTAAAGT TATGTATTCT TGGAATTATT GTAATAGTG. ..........
         25   TGTTTAAAGT TATGTATTCT TGGAATTATT GTAATAGTG. ..........
         26   TGTTTAAAGT TATGTATTCT TGGAATTATT GTAATAGTG. ..........
  Consensus   TGTTTAAAGT TATGTATTCT TGGAATTATT GTAATAGTG. ..........

201                                                 250
         21   AAAAAAAAAA AAAAAAAAAA ATTTAAAATA AAAATAAAAA ATAAGAAAAA
         22   AAAAAAAAAA AAAAAAAAAA ATTTAAAATA AAAATAAAAA ATAAGAAAAA
         23   .......... .......... .......... .......... ..........
         24   .......... .......... .......... .......... ..........
         25   .......... .......... .......... .......... ..........
         26   .......... .......... .......... .......... ..........
  Consensus   .......... .......... .......... .......... ..........

251                                                 300
         21   AAATAGTGTG CATTTTTTAT TCCCTACTTG AATCATATAT ATTTATTCTA
         22   AAATAGTGTG CATTTTTTAT TCCCTACTTG AATCATATAT ATTTATTCTA
         23   .......... .......... .......... .......... ..........
         24   .......... .......... .......... .......... ..........
         25   .......... .......... .......... .......... ..........
         26   .......... .......... .......... .......... ..........
  Consensus   .......... .......... .......... .......... ..........

301                                                 350
         21   GATATAAAAT ACTAATATGT TATTATATAT ATATATATAT TTTTTTTTTG
         22   GATATAAAAT ACTAATATGT TATTATATAT ATATATATAT TTTTTTTTTG
         23   .......... .......... .......... .......... ..........
         24   .......... .......... .......... .......... ..........
         25   .......... .......... .......... .......... ..........
         26   .......... .......... .......... .......... ..........
  Consensus   .......... .......... .......... .......... ..........
```

Figure 7B

```
              351                                                    400
      21   TGTATAGAAC GTGTGTTGTA GTTTTGAATC AAATGAAATA TCCAAGGTTA
      22   TGTATAGAAC GTGTGTTGTA GTTTTGAATC AAATGAAATA TCCAAGGTTA
      23   .......AAC GTGTGTTGTA GTTTTGAATC AAATGAAATA TCCAAGGTTA
      24   .......AAC GTGTGTTGTA GTTTTGAATC AAATGAAATA TCCAAGGTTA
      25   .......AAC GTGTGTTGTA GTTTTGAATC AAATGAAATA TCCAAGGTTA
      26   .......AAC GTGTGTTGTA GTTTTGAATC AAATGAAATA TCCAAGGTTA
Consensus  .......AAC GTGTGTTGTA GTTTTGAATC AAATGAAATA TCCAAGGTTA 401                                                    450
      21   ATTTAATAAA GAAGGAATAT TCCAGAATAT TAAGTGAAAC CGAGGCATTA
      22   ATTTAATAAA GAAGGAATAT TCCAGAATAT TAAGTGAAAC CGAGGCATTA
      23   ATTTAATAAA GAAGGAATAT TCCAGAATAT TAAGTGAAAC CGAGGCATTA
      24   ATTTAATAAA GAAGGAATAT TCCAGAATAT TAAGTGAAAC CGAGGCATTA
      25   ATTTAATAAA GAAGGAATAT TCCAGAATAT TAAGTGAAAC CGAGGCATTA
      26   ATTTAATAAA GAAGGAATAT TCCAGAATAT TAAGTGAAAC CGAGGCATTA
Consensus  ATTTAATAAA GAAGGAATAT TCCAGAATAT TAAGTGAAAC CGAGGCATTA 451                                                    500
      21   GAAAATTTGA AAGAGGAAAG TAAAAATAGA AAAGATGATG AAGAAGAAGT
      22   GAAAATTTGA AAGAGGAAAG TAAAAATAGA AAAGATGATG AAGAAGAAGT
      23   GAAAATTTGA AAGAGGAAAG TAAAAATAGA AAAGATGATG AAGAAGAAGT
      24   GAAAATTTGA AAGAGGAAAG TAAAAATAGA AAAGATGATG AAGAAGAAGT
      25   GAAAATTTGA AAGAGGAAAG TAAAAATAGA AAAGATGATG AAGAAGAAGT
      26   GAAAATTTGA AAGAGGAAAG TAAAAATAGA AAAGATGATG AAGAAGAAGT
Consensus  GAAAATTTGA AAGAGGAAAG TAAAAATAGA AAAGATGATG AAGAAGAAGT 501                                                    550
      21   AAGTTTATTT GATGGTTCTG ATGATATGGG TCGTACTTAC GATAATGATA
      22   AAGTTTATTT GATGGTTCTG ATGATATGGG TCGTACTTAC GATAATGATA
      23   AAGTTTATTT GATGGTTCTG ATGATATGGG TCGTACTTAC GATAATGATA
      24   AAGTTTATTT GATGGTTCTG ATGATATGGG TCGTACTTAC GATAATGATA
      25   AAGTTTATTT GATGGTTCTG ATGATATGGG TCGTACTTAC GATAATGATA
      26   AAGTTTATTT GATGGTTCTG ATGATATGGG TCGTACTTAC GATAATGATA
Consensus  AAGTTTATTT GATGGTTCTG ATGATATGGG TCGTACTTAC GATAATGATA 551                                                    600
      21   CATGGTCTGT ATTTAATGAA GAATGTGGTA AAAGAAAACC CAAGAAAAAG
      22   CATGGTCTGT ATTTAATGAA GAATGTGGTA AAAGAAAACC CAAGAAAAAG
      23   CATGGTCTGT ATTTAATGAA GAATGTGGTA AAAGAAAACC CAAGAAAAAG
      24   CATGGTCTGT ATTTAATGAA GAATGTGGTA AAAGAAAACC CAAGAAAAAG
      25   CATGGTCTAT ATTTAATGAA GAATGTGGTA AAAGAAAACC CAAGAAAAAG
      26   CATG...... .......... .......... .......... ..........
Consensus  CATGgtctgt atttaatgaa gaatgtggta aaagaaaacc caagaaaaag 601                                                    650
      21   CCCTAGAAAA AACCTCATCC TTTAAAAAAT AATTTCGAAT CATTCAGTTA
      22   CCCTTGAAAA AACCTCATCC TTTAAAAAAT AATTTCGAAT CATTCAGTTA
      23   CCCTAGAAAA AACCTCATCC TTTAAAAAAT AATTTCGAAT CATTCAGTTA
      24   CCCTTGAAAA AACCTCATCC TTTAAAAAAT AATTTCGAAT CATTCAGTTA
      25   CCCTTGAAAA AACCTCATCC TTTAAAAAAT AATTTCGAAT CATTCAGTTA
      26   .......... .......... .......... .......... .......TTA
Consensus  ccct.gaaaa aacctcatcc tttaaaaaat aatttcgaat cattcagTTA 651                                                    700
      21   TCAATCAAGA TATAATAGAT CAAGTATAGG TGATCTGATT CAAGTTATAA
      22   TCAATCAAGA TATAATAGAT CAAGTATAGG TGATCTGATT CAAGTTATAA
      23   TCAATCAAGA TATAATAGAT CAAGTATAGG TGATCTGATT CAAGTTATAA
      24   TCAATCAAGA TATAATAGAT CAAGTATAGG TGATCTGATT CAAGTTATAA
      25   TCAATCAAGA TATAATAGAT CAAGTATAGG TGATCTGATT CAAGTTATAA
      26   TCAATCAAGA TATAATAGAT CAAGTATAGG TGATCTGATT CAAGTTATAA
Consensus  TCAATCAAGA TATAATAGAT CAAGTATAGG TGATCTGATT CAAGTTATAA
```

Figure 7C

```
            701                                                      750
     21    AATCCACATT  TGGAGGTGAA  GATGAACATT  TATTTCAAAC  TTGTCCAGAT
     22    AATCCACATT  TGGAGGTGAA  GATGAACATT  TATTTCAAAC  TTGTCCAGAT
     23    AATCCACATT  TGGAGGTGAA  GATGAACATT  TATTTCAAAC  TTGTCCAGAT
     24    AATCCACATT  TGGAGGTGAA  GATGAACATT  TATTTCAAAC  TTGTCCAGAT
     25    AATCCACATT  TGGAGGTGAA  GATGAACATT  TATTTCAAAC  TTGTCCAGAT
     26    AATCCACATT  TGGAGGTGAA  GATGAACATT  TATTTCAAAC  TTGTCCAGAT
Consensus  AATCCACATT  TGGAGGTGAA  GATGAACATT  TATTTCAAAC  TTGTCCAGAT 751                                                      800
     21    ATTTTCGATG  AGTTAGTAAA  ACGTTCTACA  TGGGAACGTT  TGGAATTAGA
     22    ATTTTCGATG  AGTTAGTAAA  ACGTTCTACA  TGGGAACGTT  TGGAATTAGA
     23    ATTTTCGATG  AGTTAGTAAA  ACGTTCTACA  TGGGAACGTT  TGGAATTAGA
     24    ATTTTCGATG  AGTTAGTAAA  ACGTTCTACA  TGGGAACGTT  TGGAATTAGA
     25    ATTTTCGATG  AGTTAGTAAA  ACGTTCTACA  TGGGAACGTT  TGGAATTAGA
     26    ATTTTCGATG  AGTTAGTAAA  ACGTTCTACA  TGGGAACGTT  TGGAATTAGA
Consensus  ATTTTCGATG  AGTTAGTAAA  ACGTTCTACA  TGGGAACGTT  TGGAATTAGA 801                                                      850
     21    TTTGTATGAA  ACTGAAATTT  CTGATTATTT  AACTGTAACA  TATGATCTTT
     22    TTTGTATGAA  ACTGAAATTT  CTGATTATTT  AACTGTAACA  TATGATCTTT
     23    TTTGTATGAA  ACTGAAATTT  CTGATTATTT  AACTGTAACA  TATGATCTTT
     24    TTTGTATGAA  ACTGAAATTT  CTGATTATTT  AACTGTAACA  TATGATCTTT
     25    TTTGTATGAA  ACTGAAATTT  CTGATTATTT  AACTGTAACA  TATGATCTTT
     26    TTTGTATGAA  ACTGAAATTT  CTGATTATTT  AACTGTAACA  TATGATCTTT
Consensus  TTTGTATGAA  ACTGAAATTT  CTGATTATTT  AACTGTAACA  TATGATCTTT 851                                                      900
     21    CATTAAATGA  AAAAATTTTG  ACATTGAGTA  GATTAAGTAA  CGAAGAAGAT
     22    CATTAAATGA  AAAAATTTTG  ACATTGAGTA  GATTAAGTAA  CGAAGAAGAT
     23    CATTAAATGA  AAAAATTTTG  ACATTGAGTA  GATTAAGTAA  CGAAGAAGAT
     24    CATTAAATGA  AAAAATTTTG  ACATTGAGTA  GATTAAGTAA  CGAAGAAGAT
     25    CATTAAATGA  AAAAATTTTG  ACATTGAGTA  GATTAAGTAA  CGAAGAAGAT
     26    CATTAAATGA  AAAAATTTTG  ACATTGAGTA  GATTAAGTAA  CGAAGAAGAT
Consensus  CATTAAATGA  AAAAATTTTG  ACATTGAGTA  GATTAAGTAA  CGAAGAAGAT 901                                                      950
     21    TTATACAATT  TGTGGTCAGA  AATAATGAGA  AATGAAGAAA  GGAAATTTAG
     22    TTATACAATT  TGTGGTCAGA  AATAATGAGA  AATGAAGAAA  GGAAATTTAG
     23    TTATACAATT  TGTGGTCAGA  AATAATGAGA  AATGAAGAAA  GGAAATTTAG
     24    TTATACAATT  TGTGGTCAGA  AATAATGAGA  AATGAAGAAA  GGAAATTTAG
     25    TTATACAATT  TGTGGTCAGA  AATAATGAGA  AATGAAGAAA  GGAAATTTAG
     26    TTATACAATT  TGTGGTCAGA  AATAATGAGA  AATGAAGAAA  GGAAATTTAG
Consensus  TTATACAATT  TGTGGTCAGA  AATAATGAGA  AATGAAGAAA  GGAAATTTAG 951                                                      1000
     21    CTTTCTAAGA  TATCATCTAT  ATAACTACTA  TTATTCACTA  AAAAATAGAA
     22    CTTTCTAAGA  TATCATCTAT  ATAACTACTA  TTATTCACTA  AAAAATAGAA
     23    CTTTCTAAGA  TATCATCTAT  ATAACTACTA  TTATTCACTA  AAAAATAGAA
     24    CTTTCTAAGA  TATCATCTAT  ATAACTACTA  TTATTCACTA  AAAAATAGAA
     25    CTTTCTAAGA  TATCATCTAT  ATAACTACTA  TTATTCACTA  AAAAATAGAA
     26    CTTTCTAAGA  TATCATCTAT  ATAACTACTA  TTATTCACTA  AAAAATAGAA
Consensus  CTTTCTAAGA  TATCATCTAT  ATAACTACTA  TTATTCACTA  AAAAATAGAA 1001                                                     1050
     21    GCAGAGTAAG  TCGTGAATAT  TCAGAAAAAA  TATGGAATGA  ATGTGAAGAA
     22    GCAGAGTAAG  TCGTGAATAT  TCAGAAAAAA  TATGGAATGA  ATGTGAAGAA
     23    GCAGAGTAAG  TCGTGAATAT  TCAGAAAAAA  TATGGAATGA  ATGTGAAGAA
     24    GCAGAGTAAG  TCGTGAATAT  TCAGAAAAAA  TATGGAATGA  ATGTGAAGAA
     25    GCAGAGTAAG  TCGTGAATAT  TCAGAAAAAA  TATGGAATGA  ATGTGAAGAA
     26    GCAGAGTAAG  TCGTGAATAT  TCAGAAAAAA  TATGGAATGA  ATGTGAAGAA
Consensus  GCAGAGTAAG  TCGTGAATAT  TCAGAAAAAA  TATGGAATGA  ATGTGAAGAA
```

Figure 7D

```
              1051                                                    1100
       21     ACCCTTAAAA GTTTACATGA AAGTCATGAA AGTTCAATCT TTGATTTATT
       22     ACCCTTAAAA GTTTACATGA AAGTCATGAA AGTTCAATCT TTGATTTATT
       23     ACCCTTAAAA GTTTACATGA AAGTCATGAA AGTTCAATCT TTGATTTATT
       24     ACCCTTAAAA GTTTACATGA AAGTCATGAA AGTTCAATCT TTGATTTATT
       25     ACCCTTAAAA GTTTACATGA AAGTCATGAA AGTTCAATCT TTGATTTATT
       26     ACCCTTAAAA GTTTACATGA AAGTCATGAA AGTTCAATCT TTGATTTATT
Consensus     ACCCTTAAAA GTTTACATGA AAGTCATGAA AGTTCAATCT TTGATTTATT 1101                                                    1150
       21     CCATAAATGG ATTAATGGAA GTATACATGA GCTTTCGGAA TTTAAAGTTC
       22     CCATAAATGG ATTAATGGAA GTATACATGA GCTTTCGGAA TTTAAAGTTC
       23     CCATAAATGG ATTAATGGAA GTATACATGA GCTTTCGGAA TTTAAAGTTC
       24     CCATAAATGG ATTAATGGAA GTATACATGA GCTTTCGGAA TTTAAAGTTC
       25     CCATAAATGG ATTAATGGAA GTATACATGA GCTTTCGGAA TTTAAAGTTC
       26     CCATAAATGG ATTAATGGAA GTATACATGA GCTTTCGGAA TTTAAAGTTC
Consensus     CCATAAATGG ATTAATGGAA GTATACATGA GCTTTCGGAA TTTAAAGTTC 1151                                                    1200
       21     TTGTATCTGC AGGTAGATAT TCATGGAGAA ATTTACTTAA AACTGGAGAA
       22     TTGTATCTGC AGGTAGATAT TCATGGAGAA ATTTACTTAA AACTGGAGAA
       23     TTGTATCTGC AGGTAGATAT TCATGGAGAA ATTTACTTAA AACTGGAGAA
       24     TTGTATCTGC AGGTAGATAT TCATGGAGAA ATTTACTTAA AACTGGAGAA
       25     TTGTATCTGC AGGTAGATAT TCATGGAGAA ATTTACTTAA AACTGGAGAA
       26     TTGTATCTGC AGGTAGATAT TCATGGAGAA ATTTACTTAA AACTGGAGAA
Consensus     TTGTATCTGC AGGTAGATAT TCATGGAGAA ATTTACTTAA AACTGGAGAA 1201                                                    1250
       21     CGTGAATGTA AAAAATTTAT GATTAAACAT TATAAGGGTA AAACCGCTTT
       22     CGTGAATGTA AAAAATTTAT GATTAAACAT TATAAGGGTA AAACCGCTTT
       23     CGTGAATGTA AAAAATTTAT GATTAAACAT TATAAGGGTA AAACCGCTTT
       24     CGTGAATGTA AAAAATTTAT GATTAAACAT TATAAGGGTA AAACCGCTTT
       25     CGTGAATGTA AAAAATTTAT GATTAAACAT TATAAGGGTA AAACCGCTTT
       26     CGTGAATGTA AAAAATTTAT GATTAAACAT TATAAGGGTA AAACCGCTTT
Consensus     CGTGAATGTA AAAAATTTAT GATTAAACAT TATAAGGGTA AAACCGCTTT 1251   1260
       21     AAGAATTTAA
       22     AAGAATTTAA
       23     AAGAATTTAA
       24     AAGAATTTAA
       25     AAGAATTTAA
       26     AAGAATTTAA
Consensus     AAGAATTTAA
```

POLYNUCLEOTIDES AND POLYPEPTIDES INVOLVED IN GESTATIONAL MALARIA, AND BIOLOGICAL APPLICATIONS

This application is the U.S. national phase of International Application No. PCT/IB2008/051482, filed 17 Apr. 2008, which designated the U.S. and claims priority to France Application No. 07/02772, filed 17 Apr. 2007, the entire contents of each of which are hereby incorporated by reference.

The present invention relates to novel antigens involved in gestational malaria, and more particularly to polynucleotide and polypeptide sequences, conjugates, cloning vectors comprising said sequences for the preparation of immunogenic compositions and vaccines, and antibodies, and to the use thereof for treating gestational malaria. The invention also relates to diagnostic methods and kits.

Malaria is transmitted mainly by the *Plasmodium falciparum* parasite, inoculated during the bite by a mosquito, the Anopheles mosquito. Once introduced into the blood, the parasite enters the liver, where it matures before again circulating in the blood, infecting the red blood cells (erythrocytes) and multiplying.

Gestational malaria (also known as placental malaria or pregnancy-associated malaria) is observed in pregnant women. This is because, in pregnant women suffering from malaria, the placenta contains numerous infected erythrocytes. This has harmful effects on the growth of the fetus, since it disturbs exchanges between the mother and the fetus, leading to a decrease in the weight of the child at birth. In the regions of Africa where malaria is endemic, 3% to 5% of infant deaths at birth can be attributed to pregnancy associated malaria. In addition, it also presents a real danger to the mother.

The clinical severity of malaria caused by *Plasmodium falciparum* is related in part to detrimental alterations in the infected erythrocytes. These detrimental alterations are induced by the proteins of the parasite, which are exported to the surface of the erythrocytes during the development phase in the blood. Some of these surface proteins, encoded by the parasites, confer new cytoadherence properties on the erythrocytes, resulting in their removal from the bloodstream. This is because the erythrocytes are then capable of attaching to the internal wall of the blood vessels, thereby preventing the erythrocyte from traveling to the purifying organs of the immune system, one of the roles of which is to destroy cells recognized as abnormal.

The surface proteins expressed by the parasites can also undergo an antigenic variation, a phenomenon which is supposed to contribute to the fact that the parasites escape the immune system.

In regions where malaria is endemic, adults are often resistant to infections caused by *Plasmodium falciparum*. This results from gradual acquisition of immunity with respect to a wide repertoire of variant surface antigens (VSAs) of the parasite. Despite the acquisition of this immunity in adulthood, the prevalence of malaria increases during pregnancy, especially among women in their first pregnancy. Women expecting their first child lack antibodies directed against the VSAs expressed by the parasites that adhere to the placental tissues, which suggests that these parasites express new VSAs ($VSA_{PAM}$) to which these women have never previously been exposed. The parasites of pregnancy associated malaria (PAM) exhibit placental tropism and adhere to the chondroitin sulfate A (CSA) expressed at the surface of the syncytiotrophoblast layer. The women subsequently become resistant to malaria since they acquire specific antibodies against the $VSA_{PAM}$ which inhibit binding of the parasite to the CSA during subsequent pregnancies.

These observations have led the inventors to study the development of a vaccine against this form of malaria.

The study of fresh isolates, collected directly from placentas of women at the time of delivery, has enabled the inventors to identify and isolate new genes having a specificity for the parasites with placental tropism.

The present invention therefore relates to novel polynucleotides and polypeptides involved in pregnancy associated malaria, and also to the biological uses thereof as antigen-encoding sequences.

The isolated or purified polynucleotides comprising a sequence chosen from the group constituted of:
(a) a sequence having at least 80% identity with SEQ ID NO. 1,
(b) a subsequence of (a) having a minimum length of 30 nucleic acids, were studied.

SEQ ID NO. 1 corresponds to the nucleotide sequence of the hypothetical protein "PFI1785w", described during the complete sequencing of the genome of clone 3D7 of *P. falciparum*. However, no function has been associated with this hypothetical protein.

The sequence SEQ ID NO. 2 therefore corresponds to the peptide sequence of the hypothetical protein "PFI1785w".

The invention is more particularly directed toward the polynucleotides having a sequence chosen from the group constituted of:
(a) SEQ ID NO. 3,
(b) a sequence having at least 80% identity with (a),
(c) a subsequence of (a) with a minimum length of 30 nucleic acids.

SEQ ID NO. 3 corresponds to the nucleotide sequence fragment studied by the inventors and used during the implementation of one particular embodiment of the invention (see Example 1). This sequence encodes a protein given the name "NP561" by the inventors.

The invention is also directed toward the polypeptides corresponding to the abovementioned polynucleotides, and more particularly the isolated or purified polypeptides encoded by the polynucleotides above, and also the isolated or purified polypeptides comprising a sequence chosen from the group constituted of:
(a) SEQ ID NO. 4, which corresponds to the sequence of the NP561 protein,
(b) a sequence having at least 80% identity with (a),
(c) a subsequence of (a) or (b) with a minimum length of 10 amino acids.

The invention also covers the recombinant or chimeric polypeptides comprising at least one polypeptide according to the invention.

The polypeptides and the polynucleotides according to the invention are particularly suitable for use as medicaments. This is because the polypeptides according to the invention constitute pregnancy associated malaria antigens. Similarly, the polynucleotides encode antigenic proteins of this specific malaria. In this respect, they can be used as such or in a modified form as vaccines.

One suitable modification of the polypeptides according to the invention corresponds to the preparation of conjugates. Said conjugates comprise at least one polypeptide according to the invention, bound to a carrier.

The conjugates can be obtained by coupling via a covalent bond between a polypeptide and a physiologically acceptable, nontoxic, natural or synthetic carrier capable, for example, of increasing the immunogenic nature of said polypeptide.
}

With regard to the conjugates, mention will be made, by way of example, of application WO 2006/124712, which describes methods for preparing conjugates comprising a plurality of antigenic peptides of *P. falciparum*, bound to a carrier protein which improves the immunogenicity of said antigens.

The carriers that are preferred according to the invention are chosen from viral particles, lipids, for example lipids of C16-C18 type, polylysines, poly(DL-alanine)-poly (-lysine)s, nitrocellulose, polystyrene microparticles, latex bead microparticles, biodegradable polymers, polyphosphoglycan micro-particles, carrier proteins such as OPMC (outer membrane protein complex of *Neisseria meningitidis*) or improved OPMC, BSA (bovine serum albumin), TT (tetanus toxoid), ovalbumin, KLH (keyhole limpet hemocyanin), THY (bovine thyroglobulin), HbSAg and HBcAg from the hepatitis B virus, rotavirus capsid proteins, the human papilloma virus L1 protein, type 6, 11 and 16 VLP (virus like particle), tuberculin PPD (purified protein derivative), etc.

The invention is also directed toward a cloning or expression vector comprising at least one polynucleotide sequence according to the invention. The vectors covered by the invention may be phages, plasmids, cosmids or viruses.

The vector according to the invention may advantageously comprise a promoter and/or an element for regulating the expression in the host cell. In particular, the vectors may comprise sequences capable of increasing the immunogenicity of the polynucleotides and polypeptides according to the invention, for example CpG sequences, the GMCSF (Granulocyte Macrophage Colony Stimulating Factor) gene or cytokine or chemokine genes.

The transformed (or recombinant) host cells comprising at least one polynucleotide or vector according to the invention are also part of the field of the invention. These cells can be chosen from bacteria, yeasts, insect cells or mammalian cells.

The conjugates and the cloning vectors according to the invention can be advantageously used as medicaments, in particular in immunogenic compositions or vaccines.

Specifically, the cloning vector can be used as a medicament in the context of a DNA vaccination. It is in fact known that the injection of DNA (naked or inserted in a vector) into the organism can enable the expression of the corresponding proteins and result in an immune response. In this case, the polynucleotides according to the invention may be advantageously inserted into a plasmid of DNA-CSP, Nyvac pf7, VR1020, VR1012, etc., type.

The invention in fact proposes immunogenic, pharmaceutical compositions or vaccines against pregnancy associated malaria comprising at least one element chosen from the polynucleotides, the polypeptides, the conjugates or the vectors according to the invention, in combination with a pharmaceutically acceptable vehicle.

The immunogenic compositions and the vaccines may advantageously be used for immunizing animals for the purposes of obtaining antibodies, or for immunizing human beings in the context of a preventive therapy for pregnancy associated malaria.

According to one preferred embodiment, the composition or the vaccine may be adjuvanted with one or more adjuvants used in combination. Conventional adjuvants such as montanide and/or alum may be used. However, other adjuvants such as QS21, SBAS2, MF59, mLT, PHL, CpG DNA, calcium phosphate, calcium sulfate dehydrate, PLG, CT, LTB, CT/LT or AS02A are also suitable.

The immunogenic compositions and vaccines according to the invention may also comprise at least one antigen specific for *P. falciparum*, chosen from var2csa, pre-erythrocytic stage antigens (CSP, TRAP, LSA-1, LSA-3, SALSA, STARP, EXP-1), and asexual (MSP-1, MSP-3, AMA-1, EBA-175, GLURP, MSP-2, MSP-4, MSP-5, RAP-2, RESA, SERA, PfEMP-1, synthetic GPI toxin) or sexual (PfS25) erythrocytic stage antigens.

Preferably, the immunogenic composition or the vaccine may be formulated so as to be administered intradermally or intramuscularly. In this case, an advantageous dosage is from 1 to 100 µg of immunogen per injection, preferably 5 to 50 µg.

The invention also proposes monoclonal or polyclonal antibodies or antisera which specifically recognize at least one of the polypeptides and/or of the conjugates according to the invention. Advantageously, these antibodies will be recombinant, humanized or chimerized, antibodies, in particular when they are to be used as medicaments, in the context, for example, of a passive immunotherapy for pregnancy associated malaria.

The invention covers in particular the use of at least one element chosen from the polynucleotides, the polypeptides, the conjugates, the vectors and the antibodies according to the invention, for the manufacture of a medicament for use in the treatment of placental malaria.

It also proposes methods for the diagnosis, in vitro, of placental malaria in a woman who may be infected with *P. falciparum*.

According to a first method, the latter comprises the following steps:
a) bringing a tissue and/or a biological fluid, taken from the woman who may be infected, into contact, under conditions which enable an immunological reaction, with an antibody according to the invention, in order to enable the formation of immune complexes; and
b) detecting said immune complexes potentially formed.

A diagnostic kit that may advantageously be used in the context of the above method is also proposed. It comprises the following elements:
at least one antibody according to the invention,
reagents for constituting a medium suitable for a binding reaction to take place between a test sample and at least one of said antibodies, and
reagents for detecting antigen-antibody complexes produced by said binding, it being possible for these reagents to carry a label capable of being recognized by a second detection reagent.

According to one alternative method, the diagnostic method comprises the following steps:
a) bringing a tissue and/or a biological fluid, taken from the woman who may be infected, into contact, under conditions which enable an immunological reaction, with at least one element chosen from the polypeptides and the conjugates according to the invention, in order to enable the formation of immune complexes with the antibodies possibly present in said tissue and/or said biological fluid; and
b) detecting said immune complexes potentially formed.

Finally, the invention also covers the polynucleotide and polypeptide sequences of the "PFA0700c" (SEQ ID Nos. 5 and 6), "PF14_0757" (SEQ ID Nos. 7 and 8), "PFB0105c" (SEQ Nos. 9 and 10), "PF10_0351" (SEQ ID Nos. 11 and 12) and "PF10_0350" (SEQ ID Nos. 13 and 14) proteins, the sequences homologous thereto and the uses thereof as a medicament in the treatment of pregnancy associated malaria.

Other characteristics and advantages of the present invention will emerge from the description given hereinafter with reference to the attached drawings.

FIG. 1 relates to the transcription characteristics of the placental isolates. The dots indicate the log2 of the ratio of the logs of the expression (M) and of the mean intensity (A) for each group of isolates in comparison with the control (strain 3D7). Only the data that are statistically significant according to the Bonferroni correction are indicated. A single dominant var gene (var2csa) was detected in the placental isolates of all the groups examined (dots). The genes that are overexpressed or down-regulated are indicated in black when the same difference is present in the three groups, in black when the latter is present in 2 groups out of 3 (⅔) and in black when it is present in 1 group out of 3 (⅓).

FIG. 2 presents the levels of transcription of the genes identified in P. Falciparum. Indicated on the right-hand panel are the levels of transcription by 22 parasites isolated from placentas of women with pregnancy associated malaria (PW), 9 parasites derived from asymptomatic children (C) with an average age of 12, and 4 parasites from nonpregnant symptomatic women (NPW) living in the same region. Indicated on the lefthand panel are the levels of transcription of the in vitro P. falciparum strains 3D7 (diamonds), FCR3 (triangles), Hb3 (diamonds) and NF54 (squares). Each of these 4 strains was used after selection or nonselection by CSA binding using soluble CSA (3D7), BeWo cells (FCR3 and Hb3) or anti-VAR2CSA IgGs (NF54)

Figure 3:
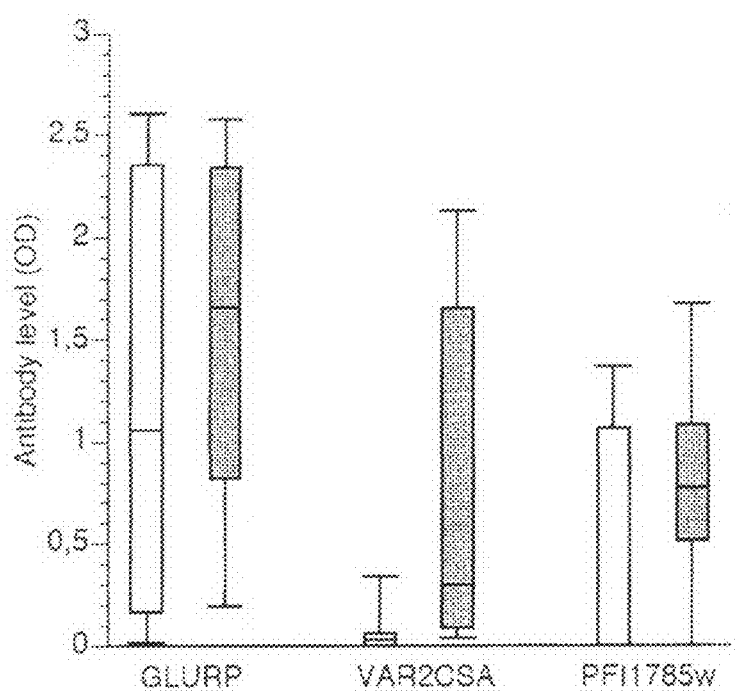

FIG. 3 illustrates the recognition, by ELISA assay, of NP561 by sera from individuals exposed to malaria. The ELISA assay was carried out on plates coated with the proteins NP561, DBL5-E of VAR2CSA and GLURP. The IgG levels, expressed as optical density, are given for exposed Ghanaian men (n=30) and pregnant women (n=30). The top and bottom lines and the lines in the middle of the rods correspond to the $75^{th}$ percentile, $25^{th}$ percentile and $50^{th}$ percentile (median) 1 respectively ·The upper and lower marks extend to the $90^{th}$ and to the $10^{th}$ percentile. The plasma concentrations of antiVAR2CSA IgG and anti-NP561 IgG are significantly higher in the pregnant woman (bars on the left represent men and on the right women).

Figure 4:
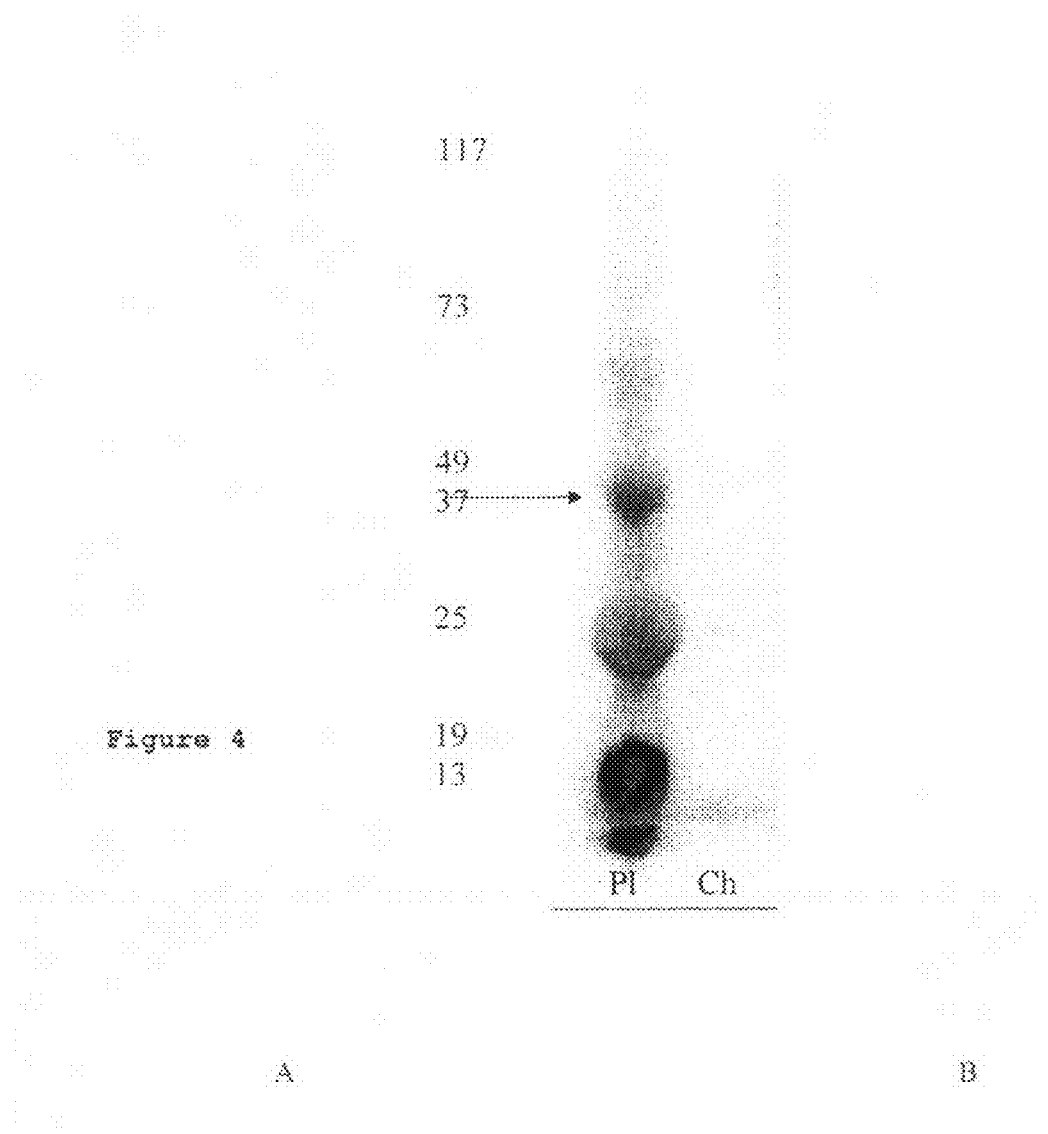

FIG. 4 describes the reactivity, detected by immunoblot, of rabbit anti-NP561 IgG with respect to SDS lyzates of erythrocytes infected with P. falciparum (PI: placental isolate, Ch: child isolate). The arrows indicate the expected size of the protein corresponding to PFI1785w.

Figure 5:
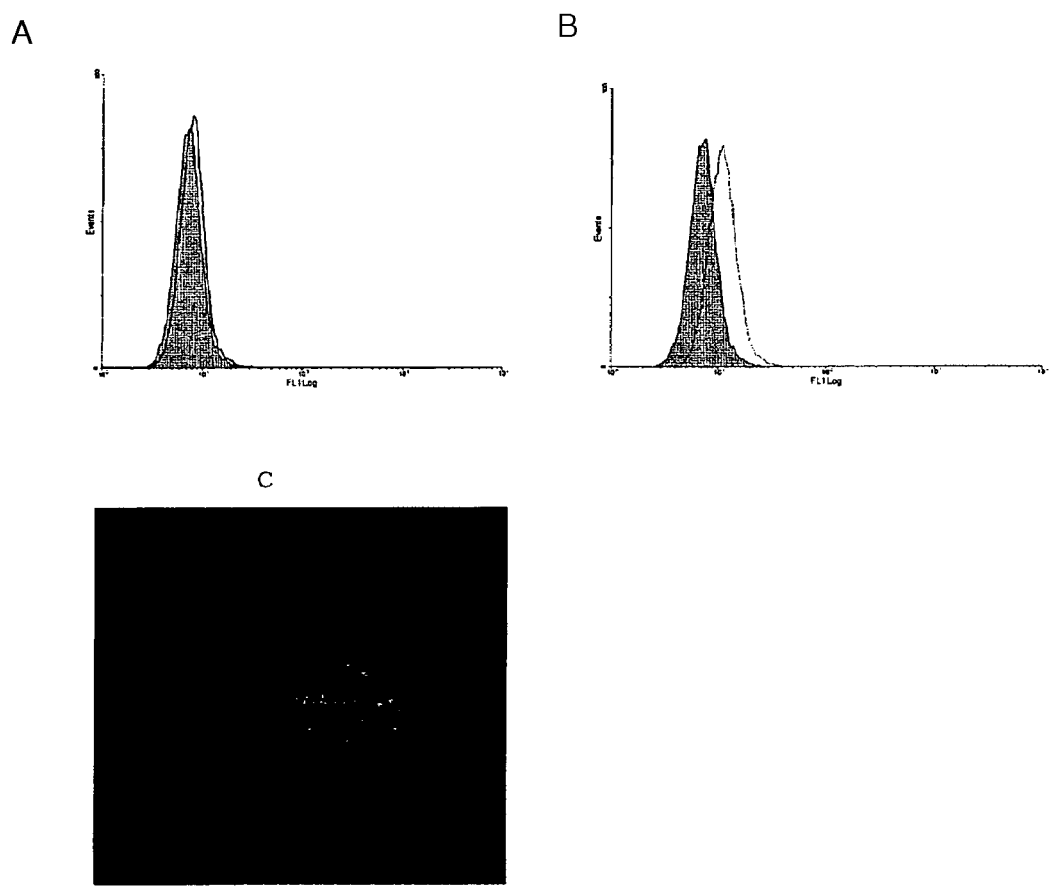

FIG. 5 shows an analysis, by flow cytometry and confocal microscopy, of erythrocytes labeled with anti-NP561 IgG or with an irrelevant control antibody. (A) Labeling of uninfected red blood cells with the anti-NP561 IgG and control of PBS-FCS on the placental parasites. (B) Labeling of the placental parasites with the anti-NP561 IgG (green line) and comparison with the negative control (PBS containing 10% of FCS). (C) Confocal microscopy of an infected placental erythrocyte labeled with an anti-NP561 antibody.

Figure 6:
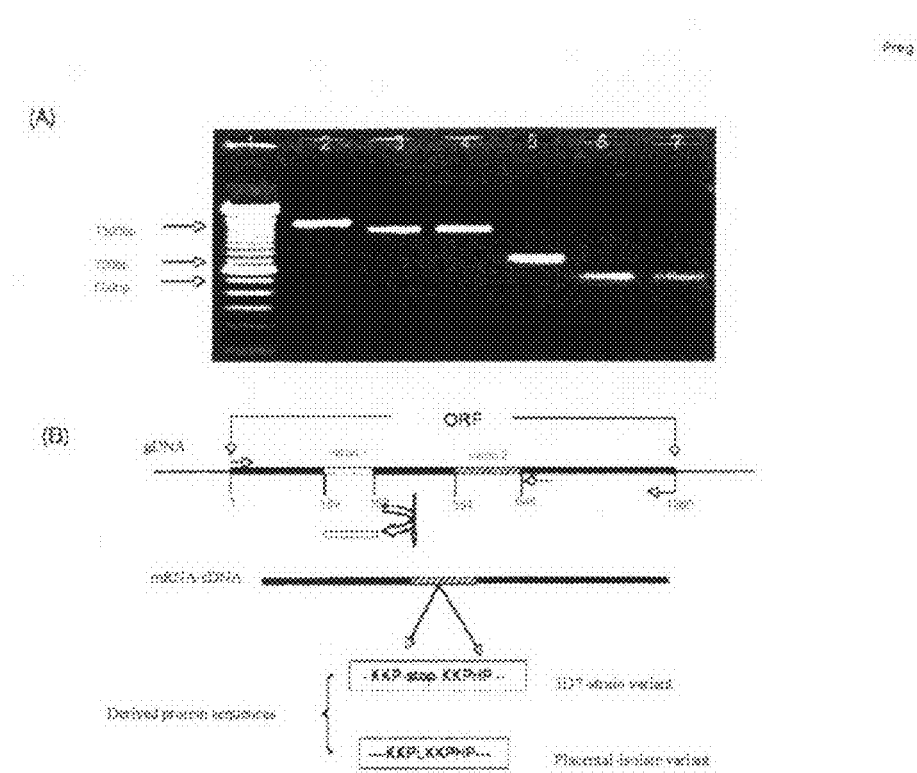

FIGS. 6A and 6B represent the PFI1785w splicing structure. FIG. 6B discloses "KKPHP" as SEQ ID NO: 19 and "KKPLKKPHP" as SEQ ID NO: 20.

FIG. 7 shows the alignments, respectively, of the sequences determined from the gDNA of the 3D7 strain (SEQ ID NO: 21); the gDNA of placental isolates (SEQ ID NO: 22); the cDNA of the 3D7 strain (SEQ ID NO: 23); the cDNA of the Senegalese placental isolate N42 (SEQ ID NO: 24); the cDNA of the Senegalese placental isolate N14 (SEQ ID NO: 25); the sequence predicted in plasmoDB from the cDNA of the 3D7 strain (SEQ ID NO: 26); and the consensus sequence.

EXAMPLE 1

Identification of New Genes Exhibiting Specificity for the Placental Tropism

Materials and Methods

Patients, sample collection and storage. The samples were collected in November 2003 in Guediawaye, in the suburbs of Dakar, Senegal. The guidelines on experiments on humans of the French and Senegalese governments were followed. This study was approved by the ethics committee of the Ministry for Health of Senegal. The nature of the project was explained to the women and their informed consent was obtained orally. Pregnant women were admitted for delivery and those for whom the thick blood smear and/or immunochromatography tests were positive for P. falciparum were enrolled.

Nonpregnant women, who presented a fever and for whom the blood smear was positive for P. falciparum were also enrolled as a control. The clinical data were recorded and 10 ml of peripheral blood were collected in heparin sodium. The red blood cells from the peripheral blood were washed 3 times and incubated in an RPMI medium at 37° C. in a candle jar (microaerophilic atmosphere) for 18-20 h enabling maturation of the ring stages to trophozoites. At delivery, a thick blood smear was prepared for a microscopic examination using placental appositions. The erythrocytes infected with P. falciparum were isolated from the positive placentas by perfusion of said placentas with 0.1% heparin sodium in PBS (phosphate buffered saline solution). The parasites were conserved in Trizol (Invitrogen) and stored at −80° C. or were deposited on Whatman paper, dried, and stored at ambient temperature, until RNA and DNA extractions. The plasma was separated from the peripheral blood and stored at −20° C. until use.

During the same period, venous blood samples were collected from infected children showing no symptoms, in the context of a transverse study carried out in parallel in the outskirts of Thies, in Senegal. The samples were collected according to the same protocols described above.

Cytoadherence tests. Bovine CSA (Sigma) and human chondroitin sulfate proteoglycans (CSPGs) were deposited, in the form of circular spots, in Falcon Petri dishes (Becton Dickinson) and the level of adhesion to CSA and to CSPG, of the placental parasites, was quantified according to the number of infected erythrocytes observed per square millimeter, estimated by examining 20 fields under a microscope at high magnification (20 times).

Culturing of parasites and selection of particular phenotypes. The P. falciparum strains were cultured according to the protocols previously described (Trager and Jensen, 1976). The 3D7 strain was synchronized with sorbitol 4 times with a gap of 8 hours in order to obtain particularly well-synchronized stages of development. The FCR3 and HB3 stages were selected according to their adhesion to CD36 or to Bewo cells. The NF54 strain was selected using antibodies specific for the PfEMP1 protein encoded by the var2csa gene. The 3D7 strain was also selected according to its adhesion to immobilized CSA. After selection, the parasites were cultured for 5 to 6 cycles in order to generate a sufficient parasite density. Enrichment in mature cells is carried out by Macs purification as previously described (Staalsoe et al., 1999). The parasites are allowed to once again contaminate new red blood cells and are subsequently recovered at 18, 36 and 44 h after invasion. The sex-specific recognition of the parasites selected was measured by flow cytometry using plasma samples from pregnant women and adult men originating from an endemic region, and also samples from nonimmune Danish volunteers (control).

Total DNA and RNA extractions. The genomic DNA was extracted from the deposits on Whatman paper using the Chelex procedure (Plowe et al., 1995). The total RNA derived from infected erythrocytes from placenta and from mature peripheral blood, containing parasites at the trophozoite/schizont stages, were prepared with Trizol. The quality of the RNA was verified with the Agilent 2100 Bioanalyzer.

msp-2 genotyping. The parasites were genotyped by analysis of the central domain of msp-2. PCR amplification was carried out as previously described (Jafary et al., 2004) using the fw (SEQ ID No. 15): 5'-GAAGGTAATTAAAACAT-TGTC-3' (5' being labeled with fluorescein) and ry (SEQ ID No. 16): 5'-GACACCTCGTCGTTGTAGGGAG-3' primers. The amplification products are passed through the ABM Prism 310 Genetic analyzer (Perkin Elmer Applied Biosystems) in order to count and quantify the fluorescent fragments.

Biochips. The biochips used in this study are described in Ralph et al., 2005. In summary, the oligonucleotide library comprises 8870 70-mers originating from the Malaria Oligo set (Qiagen-Operon) and personalized oligonucleotides, covering most of the *P. falciparum* genes. RNA samples from 18 women were assembled in three groups and the control (3D7) constituted of a mixture of various stages of development of the parasites was prepared (Table 1). The integrity of the RNA transcripts of each sample was verified with the Agilent 2100 Bioanalyzer. The labeling and the hybridization of the RNA samples were carried out according to previously described protocols (Ralph et al., 2005).

TABLE 1

|  | % rings | % trophozoites | % schizonts | number of isolates |
|---|---|---|---|---|
| group 1 | ≤5 | 70 | ≥25 | 3 |
| group 2 | ≤5 | ≥25 | 70 | 7 |
| group 3 | ≤5 | 0 | ≥95 | 8 |
| control (3D7) | 10 | 45 | 45 |  |

Data relating to the placental isolates and 3D7 examined using biochips: percentage of the state of development of each parasite as a function of the RNA group For each collection of placental parasites, a dye-swap was carried out on two technical repetitions and two biological repetitions in order to compensate for the effect of the labels and to verify the technical and biological reproducibility, thus providing four hybridized slides. Each biological repetition was analyzed separately using the R function (the R project) and the "Bioconductor package" kit (Gentleman et al., 2004) as previously described (Ralph et al., 2005). After standardization, a paired Student's t test was used to verify the points differentially expressed and the p values were then corrected using the Bonferroni method with a type 1 error of 0.05. All the $\log_2$ of the ratios of the fluorescence intensities are presented in the following manner: placental parasite set versus 3D7 control set.

Production of Primers and Real-Time Quantitative rt-PCR

The genes that were differentially expressed in vivo are compared with the expression of a control (in vitro strain 3D7), this control being composed of a mixture of parasites at various stages of development mimicking the distribution of the isolates.

For the 19 genes selected initially as a function of the level of transcription products (Table 2), probes for real-time PCR, specific for the genes, were produced on the basis of the sequences of the 3D7 line. The efficiency of the specific amplification with the primers was tested on serial dilutions of gDNA of 3 laboratory isolates (3D7, FCR3 and HB3) and 3 different field isolates. The specificity was then confirmed by analysis of the thermal denaturation curve and agarose gel electrophoresis. The var2csa-specific probes previously described were used (Tuikue Ndam et al., 2005).

TABLE 2

|  | Frequency | | | | | |
|---|---|---|---|---|---|---|
|  | 1/3 | | 2/3 | | 3/3 | |
| Up/down-regulation | up | down | up | down | up | down |
| Oligos | 178 | 243 | 25 | 29 | 43 | 21 |
| Genes | 146 | 217 | 18 | 28 | 19 | 16 |
| Hypothetical protein | 94 | 138 | 7 | 18 | 7 | 8 |

Total number of genes which are differentially expressed in in vivo parasite isolates in comparison with the in vitro control 3D7 composed of a similar mixture of parasites at various stages of development. The number of oligonucleotides used and the number of genes encoding hypothetical proteins are also indicated.

For the real-time PCR, RNA extraction in Trizol is followed by treatment for 15 min with DNase 1 (Sigma) at 37° C. The absence of DNA contaminant in the preparation was verified by means of 40 cycles of real-time PCR using primers specific for a conserved housekeeping gene (fructose-biphosphate aldolase). The DNA-free RNA was transcribed by reverse transcription using random primers with the Superscript II enzyme (Invitrogen) at 25° C. for 10 min, and then at 42° C. for 50 min, followed by a cycle at 70° C. for 15 min.

The real-time quantitative PCR was carried out on cDNA using the Rotor-Gene thermocycler system (Corbett Research) (Salanti et al., 2003). The reactions were carried out in volumes of 20 μl using Quantitect SYBR Green PCR Master Mix (Qiagen) and 0.5 mM of primers (Salanti et al., 2003). The quantitative analysis of the gene level was carried out using the Rotor-Gene software, version 4.6. The transcription product levels were compared using the ΔCt values calculated using the level of transcription of the fructose-biphosphate aldolase gene as an endogenous control.

The differences between the groups of samples studied by real-time rt-PCR were verified by means of a nonparametric test (Mann-Whitney two-sample rank sum test or Wilcoxon rank test for paired samples). The correlations were verified by means of Spearman's rank sum test. The significant limit is P=0.05. The STATA software (version 7.0, STATA Corporation) was used.

Recombinant Proteins and Immunization

The protein predicted by PlasmoDB, encoded by the PFI1785w gene of the genome of clone 3D7 of *P. falciparum*, was selected to be expressed as soluble protein. The product of this gene is a 332-amino acid protein with a transmembrane domain extending from amino acid 41 to amino acid 69 and a pexel motif located between amino acids 86 and 92. After exclusion of the transmembrane domain, the sequence ranging from base pair 391 to base pair 967 is amplified from the gDNA of 3D7 using the following primers, which include the EcoR1 and Not1 restriction sites in the 5' and 3' positions, respectively:

```
Fw (SEQ ID No. 17):
cggaattcCAATCAAGATATAATAGATCA;

Rv (SEQ ID No. 18):
atttgcggccgcCGGTTTTACCCTTATAATG.
```

The insert is cloned into the plasmid pGEX-4T-1 (Amersham Biosciences, Denmark) for the production of glutathione S-transferase-labeled recombinant protein in the *Escherichia coli* BL21 strain. The same sequence is also subcloned into the Not1 and EcoR1 restriction sites of the pBAD-TOPO vector designed in the laboratory (Barfod et al., 2006) and the recombinant proteins are produced in insect cells infected with the baculovirus and are subsequently purified as previously described (Salanti et al., 2004). The purified recombinant protein, called NP561, corresponding approximately to 70% of the complete size of the PFI1785w protein, was used as an immunogen in this study. Specific rabbit antibodies were induced as previously described (Salanti et al., 2004) and affinity-purified by means of a column to which the recombinant NP561 was attached. Briefly, NP561 was covalently coupled, via primary amine groups, to an NHS-activated sepharose HiTrap™ column, and the rabbit antibodies were purified according to the manufacturer's instructions.

Assaying of Plasma Antibodies with Respect to NP561 Using an ELISA Assay

The plasma titers of IgG specific for *P. falciparum* were measured by means of an ELISA assay using the VAR2CSA and NP561 recombinant proteins as antigens. The GLURP recombinant protein was used as control antigen. The antibody titers are expressed as optical density (OD) value.

Antibody Characterization by Immunoblotting

The samples used in this study were collected at the Korogwe district hospital, in Tanzania, in June 2006, according to the same protocols as those described above. After maturation of the parasites isolated from the peripheral blood of children, the erythrocytes infected with late trophozoite- or schizont-stage parasites are enriched by magnetic column purification (Macs) (Staalsoe et al., 1999). Protein extracts of infected erythrocytes were prepared in PBS containing 2% SDS and a complete protease inhibitor (Roche, Basle, Switzerland). The proteins derived from the isolates were revealed by means of precast NuPAGE 4-12% gradient SDS gels (Invitrogen, Tåstrup, Denmark) with a NuPAGE MOPS SDS running buffer (Invitrogen) using colored, broad-spectrum molecular weight markers (BioRad, Herlev, Denmark). After dry electrotransfer onto a polyvinylidene difluoride (PVDF) membrane in the presence of a buffer containing 20% of methanol, 25 mM of Tris and 192 mM of glycine at a pH of 8.4, the membranes are blocked with 5% of semi-skimmed milk powder diluted in a TBS-T buffer. The membranes are incubated with the rabbit antibodies directed against NP561 or against a PfEMP1 VAR4 protein, obtained before and after affinity purification, this incubation being followed by a second incubation with a second antibody conjugated to peroxidase and directed against rabbit IgGs (Sigma, MO, USA) and revealed with a solution of 3-amino-9-ethylcarbazole.

Assaying of Immunofluorescence and Flow Cytometry

The polyclonal antibodies directed against NP561 are affinity-purified from hyperimmune rabbit sera and from a group of plasma samples derived from women suffering from placental infection, and their reactivity was tested on the surface of mature infected erythrocytes derived from child isolates and from placental isolates from Tanzania. The reactivity of the antibodies with the surface of infected erythrocytes in the liquid phase was then verified by confocal microscopy, using an LSM5 microscope (Carl Zeiss MicroImaging, Inc.) (Salanti et al., 2004). The purified antibodies were also studied by flow cytometry (Staalsoe et al., 1999) as a function of the reactivity of the IgGs with the surface of intact and nonimmobilized infected erythrocytes isolated from placenta and from peripheral blood of a child from Tanzania.

Results

Identification of Genes Differentially Transcribed in PAM Parasites and Comparison with the 3D7 Control In order to evaluate the dynamic equilibrium of the levels of expression of the mRNAs of *P. falciparum* infecting pregnant women, parasites were collected from placentas of women giving birth in Senegal, as previously described (Tuikue Ndam et al., 2005). Microscopic examinations showed the predominance of red blood cells infected with late stages in all the isolates, with early ring stages generally representing less than 5% of the total population. Because of the variable distribution of the late stages (trophozoites and schizonts) in the various isolates, the samples were separated into three groups as indicated in table 1. The total RNA was isolated individually from each sample. The RNAs corresponding to all the samples of the same group were combined by mixing equal amounts of RNA. Similarly, the RNAs derived from various stages of development of the 3D7 strain were combined so as to mimic the distribution of the stages in the placental isolates. The RNA-sample groups were fluorescence-labeled and subjected to hybridization with a high-density array of oligonucleotides (Ralph et al., 2005). For each group of placental parasites, a dye-swab is carried out. The Bonferroni method, which is the most stringent, showed that 183 genes were overexpressed in the placental parasites and 261 genes were under-expressed. Among the genes overexpressed in the PAM parasites, 99 belong to group 1, 67 to group 2 and 85 to group 3. The majority of these genes (108 out of 183) correspond to hypothetical proteins. 20 of them comprise a pexel motif.

Despite the differences in distribution of the late stages of development of the parasites between the 3 RNA-sample groups, some genes constantly show the same differential expression profile in the three groups (overexpressed N=18; underexpressed N=16). These genes were generally those exhibiting the most abundant transcripts, detected both in the analyzed samples and in the 3D7 control. For some transcripts, the differential expression was detected in two of the three groups (overexpressed N=20; underexpressed N=30). However, the present analysis demonstrated that, although other var genes were also detected (in particular varCS2), var2csa was the predominant transcript overexpressed in the three groups. As exemplified by the specific and coherent transcription of var2csa, the genes which are overexpressed in more than one group, are more liable to be associated with advantageous biological elements specifically present in the parasites studied. These genes (overexpressed N=38; underexpressed N=46) are shown in table 2.

For a large number of genes identified (PAM-overexpressed N=153; 3D7-overexpressed N=234), a significant difference was only observed for one group (FIG. 1). Most of the differences observed in this category perhaps give an account of a grouping together of the expressions between the various stages of development, favored by the control used, given that many genes overexpressed in PAM were found in group 1 (predominance of trophozoites), whereas most of the genes overexpressed in 3D7 were identified in group 3 (schizonts), their expression profile also possibly exhibiting a certain specificity with respect to the in vivo and in vitro biological methods. For example, the specific overexpression, by placental parasites, of genes encoding asexual antigens such as AMA1, MSP1, MSP3, MSP5, MSP6 or EBA140, which are supposed to be involved in the invasion of red blood cells, fall into this category.

Validation of the Results on Biochips by Real-Time PCR

In order to confirm the relevance of the results on biochips, the relative quantification of the RNAs corresponding to the 19 genes differentially expressed with variations in level, as estimated with the oligonucleotide array, was carried out. The genes were chosen on the basis of the abundance of their transcripts, which varies from high to low. Additional criteria include:
  i) being constantly overexpressed in 2 of the 3 groups,
  ii) comprising at least one TM motif, pexel motif and/or signal sequence,
  iii) also being present in another biochip analysis using laboratory isolates selected for their specific phenotype.

The genes overexpressed in the PAM parasites were placed in a hierarchy (see table 2). A real-time PCR was carried out on cDNAs synthesized from the total RNAs of each group of samples and from each individual parasite sample included in the group. On the whole, the real-time PCR confirmed the data obtained on the biochips, since a good correlation between the results was obtained. Spearman's correlation test after logarithmic transformation of the data: r=0.78, p<0.0001) as indicated in table 3 below:

TABLE 3

| Gene ID | Biochips | | | rt-qPCR | | |
|---|---|---|---|---|---|---|
| | Group 1 | Group 2 | Group 3 | Group 1 | Group 2 | Group 3 |
| PFL0030c | 25.03 | 90.27 | 18.48 | 40.78 | 99.76 | 109.67 |
| PFC0110w | 40.97 | 21.55 | 19.88 | 10.66 | 18.4 | 23.15 |
| PFI1785w | 7.08 | 35.45 | 4.63 | 149.15 | 319.69 | 206.25 |
| PF10_0351 | 5.5 | 12.89 | 3.43 | 5.56 | 6.63 | 5.03 |
| PFA0700c | 5.61 | 12.74 | 3.1 | 103.7 | 171.37 | 112.99 |
| PF14_0010 | 5.61 | 3.74 | 3.54 | 10.2 | 26.48 | 5.75 |
| PF10_0344 | 8.36 | 3.39 | 2.69 | 2.76 | 3.81 | 1.91 |
| PF14_0757 | 3.31 | 2.93 | 4.59 | 2.84 | 1.63 | 0.81 |
| PFB0105c | 6.72 | 2.55 | | 3.95 | 4.4 | 4 |
| PF14_0183 | 3.85 | | 4.63 | 6.06 | 18.08 | 4.55 |
| PFB0115w | | 10.18 | | 2.41 | 4.58 | 1.54 |
| PFI1445w | 3.1 | | | 0.32 | 1.7 | 0.99 |
| MAL7P1.155 | | 2.61 | | 0.95 | 2.86 | 0.66 |
| PFL0050c | | 2.42 | | 0.69 | 2.6 | 1.04 |
| PFL1930w | | | 2.4 | 1.64 | 2.09 | 2.08 |
| PFE0325w | | | 2.32 | 1.23 | 0.8 | 0.76 |
| PF13_0304 | | | | 0.94 | 1.2 | 0.72 |
| PFL0260c | | 0.34 | 0.23 | 0.16 | 0.22 | 0.28 |
| PF10_0350 | | 0.32 | 0.17 | 0.56 | 0.61 | 0.26 |
| PFD1120c | 0.3 | 0.3 | 0.16 | 0.26 | 0.22 | 0.19 |

Confirmation by real-time quantitative PCR of the in vivo expression of cDNAs for the 19 different genes. The values are expressed as ratio relative to the control (in vitro strain 3D7) composed of a mixture of parasites at various stages of development in order to mimic that of the isolates.

Biological Validation of the Results on Biochips

Figure 2A:
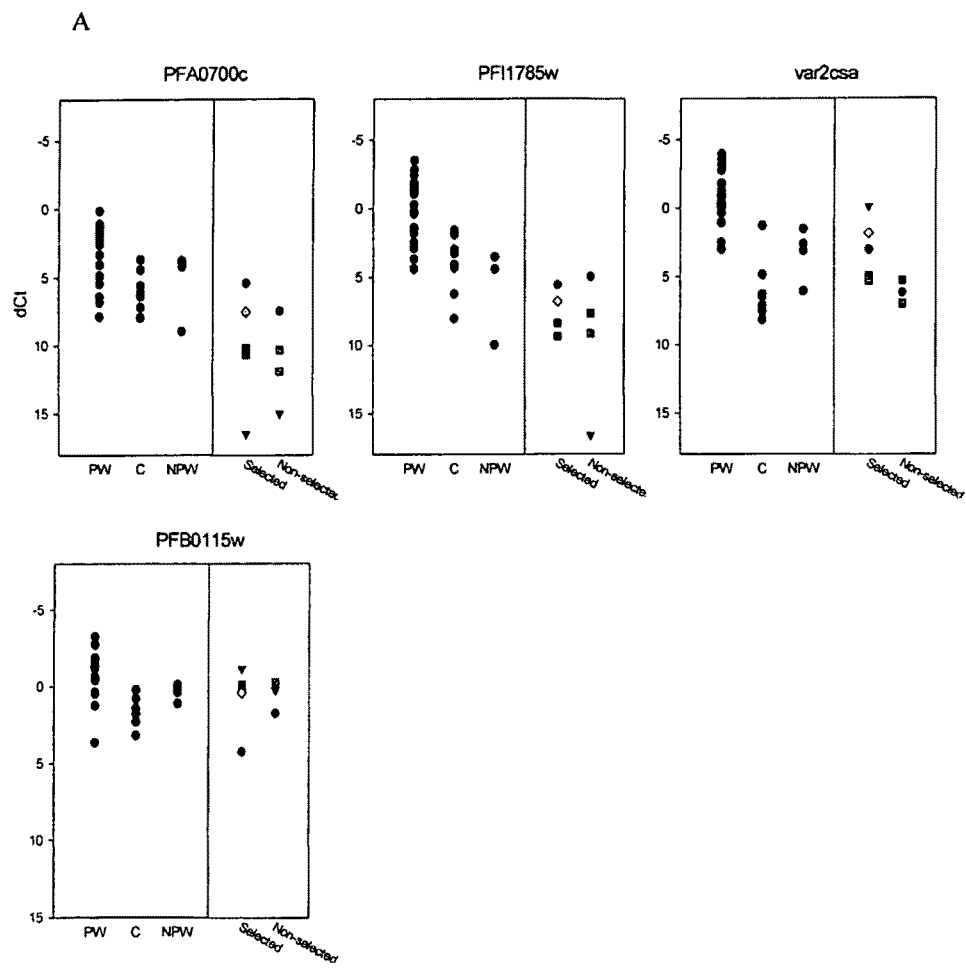
Figure 2B:
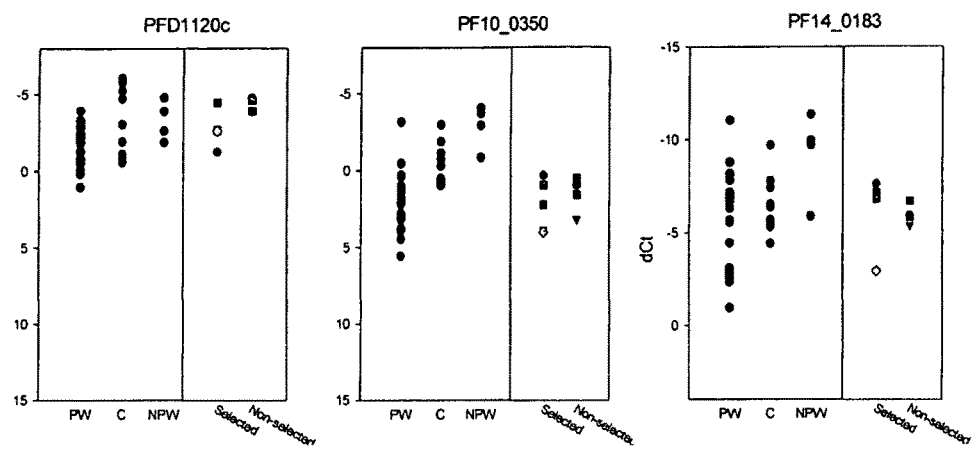
Figure 2C:
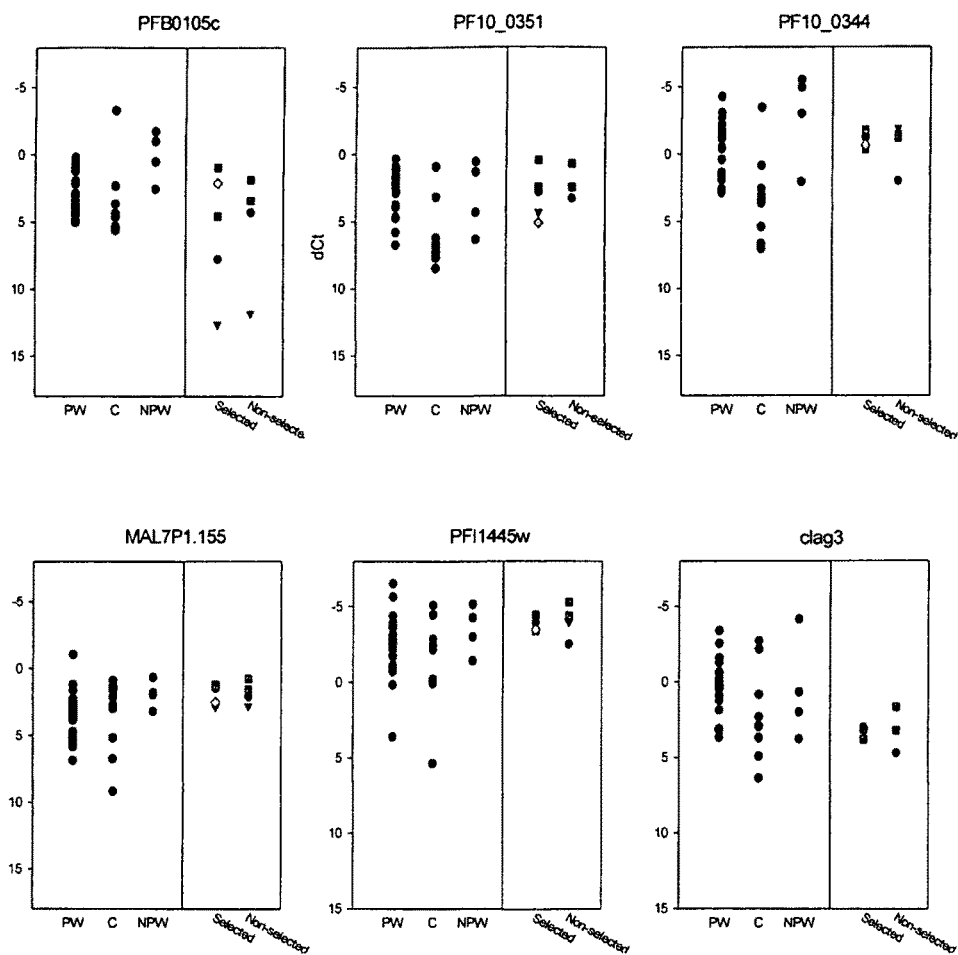

In order to verify the biological relevance of the results, the abundance of the transcripts of the 19 genes selected was determined by real-time PCR in parasites associated with various clinical presentations of malarial infection. The parasites were collected from asymptomatic children and from nonpregnant women exhibiting symptoms who were living in a geographical region close to west Senegal over a short period of time compared with the placental samples. The abundance of the transcripts corresponding to the 19 genes was measured on parasites having reached a degree of maturation and of development approximately identical to those of the parasites derived from the placentas. The abundance of the transcripts of the 19 genes was also measured on laboratory-adapted parasite lines selected for their phenotype capable or not capable of binding to CSA. As expected, var2csa exhibits a PAM-specific profile in the isolates and also a marked specificity for the laboratory isolates selected for their binding to CSA (Salanti et al., 2003) (FIG. 2, right-hand panel). By examining the transcription profiles of the parasites of various malarial syndromes, 4 transcription profile categories could be defined:
  i) strong expression in PAM parasites (shown in FIG. 2A),
  ii) strong expression in non-PAM parasites (shown in FIG. 2B),
  iii) strong expression in parasites originating from women exhibiting symptoms and from pregnant women, but not from asymptomatic children (shown in FIG. 2C),
  iv) no difference in expression among all the groups of parasites in vivo (not shown).

For all the genes grouped together in the first category except for var2csa, the specific transcription cannot be associated with CSA-binding properties exhibited by the parasite lines selected in vitro in the laboratory (FIG. 2, right-hand panel). However, one gene, PFI1785w, encoding a hypothetical protein, exhibits a profile that is clearly PAM-specific, similar to that of var2csa. Surprisingly, no difference was observed in the various laboratory-adapted in vitro lines selected for their binding-specific phenotypes, contrary to var2csa (FIG. 2, right-hand panel). PFI1785w encodes a 39.4 kD protein which is predicted to express a single molecule comprising a TM domain and a pexel sequence which directs the protein toward export. It is also predicted that the protein has a surface expression with a short N-terminal domain. The specific overexpression of this gene by placental isolates and not by non-PAM parasites, nor by in vitro laboratory lines selected for their adhesion to CSA, raises a particular interest for a more extensive characterization. On the other hand, a clear and opposite specific profile was observed for PF10_0350, which is strongly transcribed in non-PAM parasites compared with the placental parasites. The product of this gene is predicted to have a surface expression, since it possesses a transmembrane domain, but no pexel motif for the purpose of targeting to the surface of red blood cells.

Discussion

Many studies have made it possible to prove the unique nature of the antigenic and binding properties of P. falciparum-infected erythrocytes derived from placentas. A prior study of the variant surface antigens of the parasite designated the PfEMP1 variants as the major mediator of the antigenic variation and adhesion properties of the infected erythrocytes. In particular, Tuikue Ndam et al., 2005 demonstrated that VAR2CSA PfEMP1 is responsible for the CSA-binding of infected erythrocytes originating from the placenta. The present study identified differences in the expression of the genes in comparison with the parasites of the control laboratory strain 3D7, using a biochip analysis of the entire genome of P. falciparum placental parasites. This approach demonstrated the overexpression of a large number of genes by the placental parasites, which, besides var2csa, comprises genes considered to be capable of encoding surface proteins that may play a role in the biological process associated with the placental tropism of the parasites. For this first complete study of the genome of the placental parasites freshly collected in vivo, the potential errors due to the selection of the parasites by the host, to the stages of development of the parasites and to the expression of the RNA, have been minimized by virtue of (1) the sampling of patients of the same ethnic group, living in the same geographical region and having the same type of disease (placental infection), (2) the grouping together of samples according to a distribution relative to the developmental stage of the parasite, the analysis of homogeneous parasites being richer in information from the viewpoint of the properties commonly shared. This enabled the identification of genes involved in biological processes common to all the parasites that bind to CSA and preferentially develop in the placenta. The window of differentially transcribed genes is greatly reduced to 38 and 46 genes over-expressed or repressed, respectively, in the placental parasites when an additional criterion (similar observations in at least two of the three groups tested) is taken into consideration. Like var2csa, for which the over-expression was visible in the three groups of samples, the biological process may be common to contiguous stages of development of the parasite, despite the differences in expression of the genes according to these stages, as indicated by Daily et al., 2005. This suggests that these genes identified in more than one sole group may be the most relevant for controlling placental tropism in general (table 2). The transcripts representing various hypothetical proteins are differentially abundant in the isolates and in the in vitro cultures of 3D7 parasites. More extensive studies on the localization of the product of these genes and the identification of those targeted by immune responses deserve particular attention. Several of these proteins have motifs that are predicted to control their exportation out of the parasite and into the red blood cell (Marti et al., 2004). By way of example, mention will be made of the PFI1785w, PFA0700c, PF14_0757 and PF10_0351 genes (table 2). It is interesting to note that the transcription of some of these genes in the isolates collected from infected individuals also differs according to the progression of the disease, suggesting that they play a potential role in the clinical development of malaria (FIG. 2).

EXAMPLE 2

Study of the PFI1785w Gene

Immunological Characterization of the PFI1785w Gene Product

A part of the protein encoded by PFI1785w was expressed in sf9 insect cells infected with a recombinant baculovirus containing the sequence of the PFI1785w gene, and the product (NP561) was purified as a protein with a histidine tail that is secreted. NP561 was recognized in ELISA assays by serum samples originating from individuals living in endemic regions (Ghana). The sera from infected pregnant women exhibit a significantly higher titer of antibodies directed against NP561, compared with the sera from men from the same region of Ghana (p=0.04). The recognition of another recombinant parasite protein (GLURP) was also measured, and no significant difference was observed between the two types of sera with respect to this protein (FIG. 3).

The Expression of PFI1785w is Associated with the PAM Phenotype

In order to determine the localization of PFI1785w in mature erythrocytes infected with schizonts specific rabbit antisera directed against NP561 (in the form of a recombinant protein expressed in a baculovirus system) were prepared. They were used in immunoblot analyses and immunofluorescence assays (IFAs). Controls were performed using rabbit antisera directed against other, previously characterized, PfEMP1 proteins, and against uninfected erythrocytes, erythrocytes infected with laboratory strains and infected fresh erythrocytes derived from children. A protein band of approximately 40 kD, corresponding to the expected size, was specifically detected by immunoblot on placental parasite lyzates (FIG. 4). By flow cytometry, the rabbit antibodies specific for recombinant NP561 were capable of specifically labeling the surface of placenta-derived parasitized red blood cells, but not the surface of red blood cells infected with laboratory parasite strains or the surface of infected erythrocytes originating from children (FIG. 5). The surface localization of the protein corresponding to PFI1785w is clearly demonstrated by confocal microscopy after IFA. The protein is localized specifically at the surface of placenta-derived infected erythrocytes.

Discussion

PFI1785w exhibits a clearly defined profile, similar to that of var2csa, suggesting that it is PAM-specific. However, no evidence of a possible relationship with a CSA-binding phenotype was observed in the parasite lines biologically selected, in vitro, for CSA-binding. Although the CSA-binding properties represent a major specific phenotype of PAM parasites, it appears, however, that not all the characteristics of the parasites responsible for PAM can be reproduced in laboratory-adapted parasite lines. Despite the widely accepted opinion that cytoadherence is important in the development of the severe forms of the disease, there are still many aspects of this complex process that remain poorly understood. The additional studies for characterizing PFI1785w revealed that the protein encoded by this gene is expressed by the placental isolates, as is demonstrated by the western blotting analyses. By comparison with VAR2CSA, the corresponding recombinant protein (NP561) is recognized more strongly by the serum samples from pregnant women living in endemic regions for malaria, suggesting that the product of this gene is targeted by the immune response, although its relation to gender is less strong. Furthermore, specific antibodies directed against NP561 specifically label the surface of PAM parasites, as is demonstrated by the flow cytometry and the IFA. This provides evidence of an obvious involvement of this parasitic protein in the mechanism of PAM. PFI1785w is a gene having a single copy which encodes a small protein that is predicted to express a single molecule at the surface of erythrocytes. This new immunoreactive antigen that has been identified exhibits important evidence of its involvement in the mechanism that directs the placental tropism of P. falciparum, and by the same token appears to be a new priority antigen for evaluations aimed at developing an effective vaccine against PAM.

FIG. 7 gives the comparisons between genomic or cDNA nucleotide sequences of a Plasmodium strain or placental isolates.

The predicted sequence from plasmoDB, which is obtained using the cDNA of 3D7, comprises a stop cordon. The corresponding region of the intron is not translated. This sequence is therefore truncated, bases 555 to 647 being missing. This sequence can be translated from gDNA (3D7 DNA and gDNA of a Ghana isolate). The cDNAs of the N42 and N14 isolates do not have introns.

In a manner similar to PFI1785w, PFD1120c, PF10_0350 and PFLO260c are strongly transcribed in the non-PAM isolates, which evokes a possible involvement of these genes in the biological process resulting in infections of non-PAM type. PF10_0350 and PF10_0351 are contiguous and in the same orientation on chromosome 10. It is interesting to note that one is up-regulated, whereas the other is down-regulated, in the placental samples. Since there is only 1.3 kb between the stop codon of PF10_0350 and the start codon of PF10_0351, it may be supposed that the binding of the activating zone to the promoter region of PF10_0351 interferes with the enhancer of the 5' region of PF10_0350. Furthermore, FP10_0351 belongs to the family of MSP3 (merozoite surface protein 3) paralogs. It has been shown that H103, the protein encoded by PF10_0351, is expressed at the surface of merozoites (Pearce et al., 2005). The overexpression of this protein in the placental parasites may indicate that H103 acts as a virulence factor. In the present study, the differences between the in vivo parasites and the in vitro cultures of parasites are clearly demonstrated by the transcription of genes such as PFC0110w (Clag 3.2), PF10_0344 (glutamate-rich protein) and PF14_0010 (glycophorin-binding protein-related antigen). PFC0120w, which encodes a different member of the CLAG family (cytoadherence-linked asexual gene), clag 3.1, is however down-regulated in the placental parasites, this probably indicating that said gene is not involved in the in vivo pathogenesis of PAM parasites. Although the subfamily of clag genes (clag3) has been described as playing a possible role in the binding to erythrocytes during the invasion process, recent studies demonstrate that clag 3.2 transcripts, unlike clag 3.1 transcripts, cannot be detected in certain laboratory-adapted strains, such as Dd2 parasites, which is in agreement with this study. The real-time quantitative PCR of the subgroup of the 19 genes identified with DNA chips, carried out using parasites derived from individuals exhibiting different clinical forms of malarial infection, demonstrates many differences between the parasites originating from asymptomatic children and those originating from pregnant women and nonpregnant women exhibiting symptoms. These genes are: PFC0110w (clag 3.2), PF10_0344 (glurp), PFB0105c, PF10_0351 and PFI1445w. This implies differences between the parasites infecting the asymptomatic children and those infecting the individuals exhibiting symptoms. This may be in connection with the clinical form which differs between these individuals, suggesting a possible role for these proteins as a virulence factor, as has been demonstrated for clag and glurp. For some genes analyzed, no difference was observed between the isolates, but differences exist with the 3D7 line. In particular, mention will be made of PF14_0010, encoding a glycophorin-binding protein-related antigen, which was detected in the 3 groups of samples. Prior studies showed modifications in the expression of the surface-expressed proteins of P. falciparum when the parasite is maintained in culture in the long term or under the pressure of a biological or immune selection. This is perhaps also applicable to the putative virulence factors. The expression profile of the genes which were detected only in a single group of samples may potentially reflect a specificity for PAM isolates, although these genes may also be specific for some of the stages of development. The overexpression, by the placental parasites, of genes encoding multiple asexual antigens (such as AMA1, MSP1, MSP3, MSP5, MSP6 or EBA140, which are supposed to be involved in the invasion of red blood cells) is coherent with the differences between the biological processes taking place in an in vivo environment, which is rich in immune cells and in factors, and in the in vitro environment of the 3D7 strain.

PFI1785w Splicing Structure

The results obtained are represented in FIGS. 6A and 6B:
(A) shows the PCR products confirming the splicing of intron 1 and not of intron 2 in 3D7 and a placental isolate cDNA. The 3 primers represented by arrows in figure B were used to amplify a short fragment and a complete fragment from the genomic DNA of 3D7 (lanes 2 and 5), from the cDNA of 3D7 (lanes 3 and 6), and from the cDNA of a placental isolate (lanes 4 and 7). Lane 1 shows a 100 by molecular weight marker.
(B) represents the scheme of the exon/intron structure based on the predicted gene and the mRNA/cDNA. The black bars represent the predicted exons. The white and lined bars represent, respectively, intron 1 and intron 2 according to the genomic sequence of 3D7. The mRNA/cDNA scheme corresponds to the structure observed experimentally.

EXAMPLE 3

Study of the PFA0700c, PF14_0757, PFB0105c, PF10_0351 and PF10_0350 Genes

Immunological Characterization of the Gene Products

A part of the proteins encoded by PFA0700c, PF14_0757, PFB0105c, PF10_0351 and PF19_0350 was expressed in a baculovirus, transfected into insect cells and purified as a protein with a histidine tail that is secreted. The proteins were recognized in ELISA assays by serum samples originating from individuals living in endemic regions (Ghana). The sera of infected pregnant women exhibit a significantly higher titer of antibodies directed against these proteins, compared with the sera of men from the same region of Ghana (p=0.04). The recognition of another recombinant parasite protein (GLURP) was also measured, and no significant difference was observed between the two types of sera (FIG. 3).

The Expression of PFA0700c, PF14_0757, PFB0105c, PF10_0351 and PF10_0350 is Associated with the PAM Phenotype In order to determine the localization of PFA0700c, PF14_0757, PFB0105c, PF10_0351 and PF10_0350 in mature erythrocytes infected with schizonts, specific rabbit antisera directed against these proteins (in the form of a recombinant protein expressed in a baculovirus system) were prepared. They were used in immunoblot analyses and in immunofluorescence labeling (IFA). Controls were performed using rabbit antisera directed against other surface proteins such as PfEMP1 previously characterized, and against uninfected erythrocytes, erythrocytes infected with laboratory strains and infected fresh erythrocytes derived from children. Protein bands of approximately 13 kD, 25 kD, 35 kD, 65 kD and 82 kD, corresponding to the respective sizes expected, were specifically detected by immunoblotting on placental parasite lyzates. By flow cytometry, the rabbit antibodies specific for these recombinant proteins were capable of specifically labeling the surface of placenta-derived parasitized red blood cells, but not the surface of red blood cells infected with laboratory parasite strains or the surface of infected erythrocytes originating from children. The surface localization of the proteins corresponding to PFA0700c, PF14_0757, PFB0105c, PF10_0351 and PF10_0350 was verified by confocal microscopy after IFA. The antibodies specific for each of the above proteins were used in immunoprecipitation on lyzates of parasitized red blood cells desequested from placentas. The protein complexes were dissociated and analyzed by mass spectrometry. The combination of all these methods enabled us to confirm the expression, the exportation to the surface of the parasitized red blood cell and the antigenicity of new parasitic proteins involved in the pathogenesis of pregnancy-associated malaria. These proteins constitute therapeutic and vaccine targets of great importance.

Example 4

Preparation of an Antibody Directed Against the NP561 Protein

Rabbits are immunized using incomplete/complete Freund's adjuvant. This adjuvant helps to induce the production of reactive antibodies directed against NP561. The NP561-specific IgG titers are detected by ELISA assay, and increase as the immunizations proceed, and reach a maximum after 5 immunizations (Barfod et al., 2006). The polyclonal antibodies directed against NP561 are affinity-purified from the sera of hyperimmune rabbits.

References

Trager W, Jensen J B (1976) Human malaria parasites in continuous culture. Science 193: 673-675.

Staalsoe T, Giha H A, Dodoo D, Theander T G, Hviid L (1999) Detection of antibodies to variant antigens on *Plasmodium falciparum*-infected erythrocytes by flow cytometry. Cytometry 35: 329-336.

Plowe C V, Djimde A, Bouare M, Doumbo O, Wellems T E (1995) Pyrimethamine and proguanil resistance-conferring mutations in *Plasmodium falciparum* dihydrofolate reductase: polymerase chain reaction methods for surveillance in Africa. Am J Trop Med Hyg 52: 565-568.

Jafari S, Le Bras J, Bouchaud O, Durand R (2004) *Plasmodium falciparum* clonal population dynamics during malaria treatment. J Infect Dis 189: 195-203.

Ralph S A, Bischoff E, Mattei D, Sismeiro O, Dillies M A, et al. (2005) Transcriptome analysis of antigenic variation in *Plasmodium falciparum*—var silencing is not dependent on antisense RNA. Genome Biol 6: R93.

Gentleman R C, Carey V J, Bates D M, Bolstad B, Dettling M, et al. (2004) Bioconductor: open software development for computational biology and bioinformatics. Genome Biol 5: R80.

Tuikue Ndam N G, Salanti A, Bertin G, Dahlback M, Fievet N, et al. (2005) High Level of var2csa Transcription by *Plasmodium falciparum* Isolated from the Placenta. J Infect Dis 192: 331-335.

Salanti A, Staalsoe T, Laystsen T, Jensen A T, Sowa M P, et al. (2003) Selective upregulation of a single distinctly structured var gene in chondroitin sulphate A-adhering *Plasmodium falciparum* involved in pregnancy-associated malaria. Mol Microbiol 49: 179-191.

Salanti A, Dahlback M, Turner L, Nielsen M A, Barfod L, et al. (2004) Evidence for the involvement of VAR2CSA in pregnancy-associated malaria. J Exp Med 200: 1197-1203.

Pearce J A, Mills K, Triglia T, Cowman A F, Anders R F (2005) Characterisation of two novel proteins from the asexual stage of *Plasmodium falciparum*, H101 and H103. Mol Biochem Parasitol 139: 141-151.

Marti M, Good R T, Rug M, Knuepfer E, Cowman A F (2004) Targeting malaria virulence and remodeling proteins to the host erythrocyte. Science 306: 1930-1933.

Daily J P, Le Roch K G, Sarr O, Ndiaye D, Lukens A, et al. (2005) In vivo transcriptome of *Plasmodium falciparum* reveals overexpression of transcripts that encode surface proteins. J Infect Dis 191: 1196-1203.

Barfod L, Nielsen M A, Turner L, Dahlback M, Jensen A T, Hviid L, Theander T G, Salanti A. (2006) Baculovirus-expressed constructs induce immunoglobulin G that recognizes VAR2CSA on *Plasmodium falciparum*-infected erythrocytes. Infect Immun 74:4357-60.

---

The invention claimed is:

1. An isolated or purified polypeptide encoded by the polynucleotide consisting of SEQ ID NO. 3

2. A recombinant polypeptide encoded by the polynucleotide consisting of SEQ ID NO:3.

3. A medicament comprising a polypeptide of claim 1.

4. A conjugate comprising a carrier and a polypeptide wherein the polypeptide is encoded by the polynucleotide consisting of SEQ ID NO:3.

5. A composition comprising the conjugate of claim 4 and a vehicle.

6. An immunogenic composition comprising a polypeptide of claim 1, in combination with a pharmaceutically acceptable vehicle.

7. The immunogenic composition of claim 6, further comprising at least one P. falciparum antigen chosen from var2csa, pre-erythrocytic stage antigens, and asexual or sexual erythrocytic stage antigens.

8. The conjugate of claim 4 wherein the carrier is a physiologically acceptable, nontoxic, natural or synthetic carrier.

9. The conjugate of claim 4 wherein the carrier is selected from the group consisting of a viral particle, a lipid, a polylysine, a poly (DL-alanine)-poly(-lysine), nitrocellulose, polystyrene, a microparticle, a biodegradable polymer, an outer membrane protein complex of Neisseria meningitides, bovine serum albumin, tetanus toxoid, ovalbumin, keyhole limpet hemocyanin, bovine thyroglobulin, a HbSAg from hepatitis B virus, a HBcAg from hepatitis B virus, a rotavirus capsid protein, a human papilloma virus L1 protein, type 6, 11 and 16 virus-like particles, and a tuberculin purified protein derivative.

10. The conjugate of claim 9 wherein the carrier is selected from the group consisting of a latex bead microparticle and a polyphosphoglycan microparticle.

* * * * *

SEQUENCE LISTING

```
<160> NUMBER OF SEQ ID NOS: 26

<210> SEQ ID NO 1
<211> LENGTH: 999
<212> TYPE: DNA
<213> ORGANISM: Plasmodium falciparum

<400> SEQUENCE: 1
atgtggtttt gtaataaatt taatgataat acaactaaag ggttactgga ttctaataat     60
gtacaatcaa aatattgtac catatattct tttgatgatg aagaaaataa tacgaaaaga    120
aaaaatcagt tcgcatcttt tagtaaatta tgtttaaagt tatgtattct tggaattatt    180
gtaatagtga acgtgtgttg tagttttgaa tcaaatgaaa tatccaaggt taatttaata    240
aagaaggaat attccagaat attaagtgaa accgaggcat tagaaaattt gaaagaggaa    300
agtaaaaata gaaaagatga tgaagaagaa gtaagtttat ttgatggttc tgatgatatg    360
ggtcgtactt acgataatga tacatgttat caatcaagat ataatagatc aagtataggt    420
gatctgattc aagttataaa atccacattt ggaggtgaag atgaacattt atttcaaact    480
tgtccagata ttttcgatga gttagtaaaa cgttctacat gggaacgttt ggaattagat    540
ttgtatgaaa ctgaaatttc tgattattta actgtaacat atgatctttc attaaatgaa    600
aaaattttga cattgagtag attaagtaac gaagaagatt tatacaattt gtggtcagaa    660
ataatgagaa atgaagaaag gaaatttagc tttctaagat atcatctata taactactat    720
tattcactaa aaaatagaag cagagtaagt cgtgaatatt cagaaaaaat atggaatgaa    780
tgtgaagaaa cccttaaaag tttacatgaa agtcatgaaa gttcaatctt tgatttattc    840
cataaatgga ttaatggaag tatacatgag ctttcggaat ttaaagttct tgtatctgca    900
ggtagatatt catggagaaa tttacttaaa actggagaac gtgaatgtaa aaaatttatg    960
```

```
attaaacatt ataagggtaa aaccgcttta agaatttaa                    999
```

<210> SEQ ID NO 2
<211> LENGTH: 332
<212> TYPE: PRT
<213> ORGANISM: Plasmodium falciparum

<400> SEQUENCE: 2

```
Met Trp Phe Cys Asn Lys Phe Asn Asp Asn Thr Thr Lys Gly Leu Leu
1               5                   10                  15

Asp Ser Asn Asn Val Gln Ser Lys Tyr Cys Thr Ile Tyr Ser Phe Asp
            20                  25                  30

Asp Glu Glu Asn Asn Thr Lys Arg Lys Asn Gln Phe Ala Ser Phe Ser
        35                  40                  45

Lys Leu Cys Leu Lys Leu Cys Ile Leu Gly Ile Ile Val Ile Val Asn
    50                  55                  60

Val Cys Cys Ser Phe Glu Ser Asn Glu Ile Ser Lys Val Asn Leu Ile
65                  70                  75                  80

Lys Lys Glu Tyr Ser Arg Ile Leu Ser Glu Thr Glu Ala Leu Glu Asn
                85                  90                  95

Leu Lys Glu Glu Ser Lys Asn Arg Lys Asp Asp Glu Glu Val Ser
            100                 105                 110

Leu Phe Asp Gly Ser Asp Asp Met Gly Arg Thr Tyr Asp Asn Asp Thr
        115                 120                 125

Cys Tyr Gln Ser Arg Tyr Asn Arg Ser Ser Ile Gly Asp Leu Ile Gln
    130                 135                 140

Val Ile Lys Ser Thr Phe Gly Gly Glu Asp Glu His Leu Phe Gln Thr
145                 150                 155                 160

Cys Pro Asp Ile Phe Asp Glu Leu Val Lys Arg Ser Thr Trp Glu Arg
                165                 170                 175

Leu Glu Leu Asp Leu Tyr Glu Thr Glu Ile Ser Asp Tyr Leu Thr Val
            180                 185                 190

Thr Tyr Asp Leu Ser Leu Asn Glu Lys Ile Leu Thr Leu Ser Arg Leu
        195                 200                 205

Ser Asn Glu Glu Asp Leu Tyr Asn Leu Trp Ser Glu Ile Met Arg Asn
    210                 215                 220

Glu Glu Arg Lys Phe Ser Phe Leu Arg Tyr His Leu Tyr Asn Tyr Tyr
225                 230                 235                 240

Tyr Ser Leu Lys Asn Arg Ser Arg Val Ser Arg Glu Tyr Ser Glu Lys
                245                 250                 255

Ile Trp Asn Glu Cys Glu Glu Thr Leu Lys Ser Leu His Glu Ser His
            260                 265                 270

Glu Ser Ser Ile Phe Asp Leu Phe His Lys Trp Ile Asn Gly Ser Ile
        275                 280                 285

His Glu Leu Ser Glu Phe Lys Val Leu Val Ser Ala Gly Arg Tyr Ser
    290                 295                 300

Trp Arg Asn Leu Leu Lys Thr Gly Glu Arg Glu Cys Lys Lys Phe Met
305                 310                 315                 320

Ile Lys His Tyr Lys Gly Lys Thr Ala Leu Arg Ile
                325                 330
```

<210> SEQ ID NO 3
<211> LENGTH: 595
<212> TYPE: DNA
<213> ORGANISM: Unknown
<220> FEATURE:

<223> OTHER INFORMATION: Description of Unknown: NP561 encoding
sequence

<400> SEQUENCE: 3

```
caatcaagat ataatagatc aagtataggt gatctgattc aagttataaa atccacattt      60
ggaggtgaag atgaacattt atttcaaact tgtccagata ttttcgatga gttagtaaaa     120
cgttctacat gggaacgttt ggaattagat ttgtatgaaa ctgaaatttc tgattattta     180
actgtaacat atgatctttc attaaatgaa aaaattttga cattgagtag attaagtaac     240
gaagaagatt tatacaattt gtggtcagaa ataatgagaa atgaagaaag gaaatttagc     300
tttctaagat atcatctata taactactat tattcactaa aaaatagaag cagagtaagt     360
cgtgaatatt cagaaaaaat atggaatgaa tgtgaagaaa cccttaaaag tttacatgaa     420
agtcatgaaa gttcaatctt tgatttattc cataaatgga ttaatggaag tatacatgag     480
ctttcggaat ttaaagttct tgtatctgca ggtagatatt catggagaaa tttacttaaa     540
actggagaac gtgaatgtaa aaaatttatg attaaacatt ataagggtaa aaccg          595
```

<210> SEQ ID NO 4
<211> LENGTH: 198
<212> TYPE: PRT
<213> ORGANISM: Unknown
<220> FEATURE:
<223> OTHER INFORMATION: Description of Unknown: NP561
sequence

<400> SEQUENCE: 4

```
Gln Ser Arg Tyr Asn Arg Ser Ser Ile Gly Asp Leu Ile Gln Val Ile
 1               5                  10                  15

Lys Ser Thr Phe Gly Gly Glu Asp Glu His Leu Phe Gln Thr Cys Pro
            20                  25                  30

Asp Ile Phe Asp Glu Leu Val Lys Arg Ser Thr Trp Glu Arg Leu Glu
        35                  40                  45

Leu Asp Leu Tyr Glu Thr Glu Ile Ser Asp Tyr Leu Thr Val Thr Tyr
    50                  55                  60

Asp Leu Ser Leu Asn Glu Lys Ile Leu Thr Leu Ser Arg Leu Ser Asn
65                  70                  75                  80

Glu Glu Asp Leu Tyr Asn Leu Trp Ser Glu Ile Met Arg Asn Glu Glu
                85                  90                  95

Arg Lys Phe Ser Phe Leu Arg Tyr His Leu Tyr Asn Tyr Tyr Tyr Ser
            100                 105                 110

Leu Lys Asn Arg Ser Arg Val Ser Arg Glu Tyr Ser Glu Lys Ile Trp
        115                 120                 125

Asn Glu Cys Glu Glu Thr Leu Lys Ser Leu His Glu Ser His Glu Ser
    130                 135                 140

Ser Ile Phe Asp Leu Phe His Lys Trp Ile Asn Gly Ser Ile His Glu
145                 150                 155                 160

Leu Ser Glu Phe Lys Val Leu Val Ser Ala Gly Arg Tyr Ser Trp Arg
                165                 170                 175

Asn Leu Leu Lys Thr Gly Glu Arg Glu Cys Lys Lys Phe Met Ile Lys
            180                 185                 190

His Tyr Lys Gly Lys Thr
        195
```

<210> SEQ ID NO 5
<211> LENGTH: 333
<212> TYPE: DNA
<213> ORGANISM: Plasmodium falciparum -continued

<400> SEQUENCE: 5

```
atgtcgtttt attattttaa attatcattc atttctattt tactgtgtat tttaataatt    60
acacataagt tcagccttga acaaataact cataataaaa gtaataattt taatattata   120
aatgtaacac acaggagatt actagccgaa ccacacaaat cacatatatt gaaaacccat   180
aaaggagaaa attcaatggc acaaccaata gttaataaat taagagaaaa tcatacagag   240
tgtcctaaaa aatcatcttc cattaagctt aaaaaaattt taatacttgt atctttgttt   300
acattacctt gttctttctt ttgttttcaa taa                                333
```

<210> SEQ ID NO 6
<211> LENGTH: 110
<212> TYPE: PRT
<213> ORGANISM: Plasmodium falciparum

<400> SEQUENCE: 6

```
Met Ser Phe Tyr Tyr Phe Lys Leu Ser Phe Ile Ser Ile Leu Leu Cys
1               5                   10                  15
Ile Leu Ile Ile Thr His Lys Phe Ser Leu Glu Gln Ile Thr His Asn
            20                  25                  30
Lys Ser Asn Asn Phe Asn Ile Ile Asn Val Thr His Arg Arg Leu Leu
        35                  40                  45
Ala Glu Pro His Lys Ser His Ile Leu Lys Thr His Lys Gly Glu Asn
    50                  55                  60
Ser Met Ala Gln Pro Ile Val Asn Lys Leu Arg Glu Asn His Thr Glu
65                  70                  75                  80
Cys Pro Lys Lys Ser Ser Ser Ile Lys Leu Lys Lys Ile Leu Ile Leu
                85                  90                  95
Val Ser Leu Phe Thr Leu Pro Cys Ser Phe Phe Cys Phe Gln
            100                 105                 110
```

<210> SEQ ID NO 7
<211> LENGTH: 636
<212> TYPE: DNA
<213> ORGANISM: Plasmodium falciparum

<400> SEQUENCE: 7

```
atgaaatttt tttctgttat gcaaatattt ttaaatttgt taacaattag tgggatttta    60
ttattaaata taataatatg tgacaaaagt gaaacaatgt attcaggagt ttatcatata   120
tatatatata gaagaaattt gtctgagtca aaaagtgtaa agaataaagg attaagaaat   180
aaagtgaga aaataaaatt aaaaaatgga gtcgatgaaa aaaatgatag tactcctctt   240
aatctttata acatatggtc acctgctttg ggtatagcta aaaacgcatt tgatgagatg   300
ataaaagatt tatggcttta tagaagat tatttaaata aatatgaata tcaacgttat   360
catcatatta tgtgtaggag acctgtatgt gtaagaatta ataccgtac attgtataaa   420
tcaaaagatg atattggtgt tgcactatca tctacagata tgcaacatac tcttaatttt   480
tatagttggg ttaaaaatgg agaatcaatt gatgaaatga aaaaatttat ttattcatat   540
ataaagtgtt atgatacatt acaaaatgat ttatttaatg aacataggaa aatatgtaca   600
ggaagggtga ggaattccaa aggattagat atgtaa                            636
```

<210> SEQ ID NO 8
<211> LENGTH: 211
<212> TYPE: PRT
<213> ORGANISM: Plasmodium falciparum

<400> SEQUENCE: 8

```
Met Lys Phe Phe Ser Val Met Gln Ile Phe Leu Asn Leu Leu Thr Ile
1               5                   10                  15

Ser Gly Ile Leu Leu Asn Ile Ile Cys Asp Lys Ser Glu Thr
            20                  25                  30

Met Tyr Ser Gly Val Tyr His Ile Tyr Ile Tyr Arg Arg Asn Leu Ser
            35                  40                  45

Glu Ser Lys Ser Val Lys Asn Lys Gly Leu Arg Asn Lys Ser Glu Lys
        50                  55                  60

Asn Lys Leu Lys Asn Gly Val Asp Glu Lys Asn Asp Ser Thr Pro Leu
65                  70                  75                  80

Asn Leu Tyr Asn Ile Trp Ser Pro Ala Leu Gly Ile Ala Lys Asn Ala
                85                  90                  95

Phe Asp Glu Met Ile Lys Asp Leu Trp Leu Tyr Ile Glu Asp Tyr Leu
            100                 105                 110

Asn Lys Tyr Glu Tyr Gln Arg Tyr His His Ile Met Cys Arg Arg Pro
        115                 120                 125

Val Cys Val Arg Ile Lys Tyr Arg Thr Leu Tyr Lys Ser Lys Asp Asp
130                 135                 140

Ile Gly Val Ala Leu Ser Ser Thr Asp Met Gln His Thr Leu Asn Phe
145                 150                 155                 160

Tyr Ser Leu Val Lys Asn Gly Glu Ser Ile Asp Glu Met Lys Lys Phe
                165                 170                 175

Ile Tyr Ser Tyr Ile Lys Cys Tyr Asp Thr Leu Gln Asn Asp Leu Phe
            180                 185                 190

Asn Glu His Arg Lys Ile Cys Thr Gly Arg Val Arg Asn Ser Lys Gly
        195                 200                 205

Leu Asp Met
    210
```

<210> SEQ ID NO 9
<211> LENGTH: 908
<212> TYPE: DNA
<213> ORGANISM: Plasmodium falciparum

<400> SEQUENCE: 9

```
atgtggttat gcaaaagggg actgagtgtt aatgatacaa ctaaatgtga tgttccatgt     60
aaagattttt acatgttatt tttaagtaat aaaaaagaga aattaaatg ggaacatttt    120
ttggttatat cttttaagt aaatttatga aattgtcaat ttctcttctt ttacttgcat    180
taattcagaa tatactatta agcaatgttt ctttaatttc tggatcacac ttatataaga    240
gaaattcaag aaaatttgct gagggatata tgaaggatc tggatcagaa aaaaatgtat    300
atctttcaaa taaaaataaa gaattaata tgaaccaaca atcagataat aaaatgtgtg    360
atgaatgtga tgatatgaat caaccaggag atgtaaataa aatgacaaa acatcaaatg    420
atcaagcaaa ttcaagtgat tctgattgtg agcccttacc atttggatta aaaccttcag    480
atttaaatag aaaagttaca gaagaagatt tagaaagaat gataatagaa ttaccaggaa    540
aattagaaag gaaagatatg tatttaatat ggcattatag tcattctctt ttgagagata    600
aatttaataa aatgaaaagt tcgttatgga gtatttgtgg gaaattagct catgaacata    660
agttaccatt caaaattaaa atgaagaaat ggtggaaatg ttgtggtcat gttacagatg    720
aattattaat aaaagagcat gatgattata attctatata taattatatt ataatgaat    780
catcaagtcg tgaacaattt cttatatttc ttaatatgat aaagcattca tggacaacat    840
```

```
ttactatgga gactttatt aaatgtaaga tttctttaga aaataacatg agaaatgtta      900
caaattaa                                                             908
```

<210> SEQ ID NO 10
<211> LENGTH: 302
<212> TYPE: PRT
<213> ORGANISM: Plasmodium falciparum
<400> SEQUENCE: 10

```
Met Trp Leu Cys Lys Arg Gly Leu Ser Val Asn Asp Thr Thr Lys Cys
1               5                   10                  15

Asp Val Pro Cys Lys Asp Phe Tyr Met Leu Phe Leu Ser Asn Lys Lys
            20                  25                  30

Glu Lys Ile Lys Cys Gly Thr Phe Phe Gly Tyr Ile Phe Leu Ser Lys
        35                  40                  45

Phe Met Lys Leu Ser Ile Ser Leu Leu Leu Ala Leu Ile Gln Asn
    50                  55                  60

Ile Leu Leu Ser Asn Val Ser Leu Ile Ser Gly Ser His Leu Tyr Lys
65                  70                  75                  80

Arg Asn Ser Arg Lys Phe Ala Glu Gly Tyr Met Lys Gly Ser Gly Ser
                85                  90                  95

Glu Lys Asn Val Tyr Leu Ser Asn Lys Asn Lys Glu Ile Asn Met Asn
            100                 105                 110

Gln Gln Ser Asp Asn Lys Met Cys Asp Glu Cys Asp Asp Met Asn Gln
        115                 120                 125

Pro Gly Asp Val Asn Lys Asn Asp Lys Thr Ser Asn Asp Gln Ala Asn
    130                 135                 140

Ser Ser Asp Ser Asp Cys Glu Pro Leu Pro Phe Gly Leu Lys Pro Ser
145                 150                 155                 160

Asp Leu Asn Arg Lys Val Thr Glu Glu Asp Leu Glu Arg Met Ile Ile
                165                 170                 175

Glu Leu Pro Gly Lys Leu Glu Arg Lys Asp Met Tyr Leu Ile Trp His
            180                 185                 190

Tyr Ser His Ser Leu Leu Arg Asp Lys Phe Asn Lys Met Lys Ser Ser
        195                 200                 205

Leu Trp Ser Ile Cys Gly Lys Leu Ala His Glu His Lys Leu Pro Phe
    210                 215                 220

Lys Ile Lys Met Lys Lys Trp Trp Lys Cys Cys Gly His Val Thr Asp
225                 230                 235                 240

Glu Leu Leu Ile Lys Glu His Asp Asp Tyr Asn Ser Ile Tyr Asn Tyr
                245                 250                 255

Ile Asn Asn Glu Ser Ser Ser Arg Glu Gln Phe Leu Ile Phe Leu Asn
            260                 265                 270

Met Ile Lys His Ser Trp Thr Thr Phe Thr Met Glu Thr Phe Ile Lys
        275                 280                 285

Cys Lys Ile Ser Leu Glu Asn Asn Met Arg Asn Val Thr Asn
    290                 295                 300
```

<210> SEQ ID NO 11
<211> LENGTH: 1699
<212> TYPE: DNA
<213> ORGANISM: Plasmodium falciparum
<400> SEQUENCE: 11

```
atgttgaata ttttaatat aattttcttg ttgttttaa taaacatata tatatgtgaa      60
gccaatggaa cactctctga aaatattgaa agtgctgaag agatagatgc tttaaaaacg    120
```

```
aatttaagaa atggatattt aaataatact tattttaatg aagaaaacaa taatttaaat      180
atagaaaatg aaataaataa tacaaattat aatgaagtaa cagaagaaac taagaagaa       240 ttatatgata taaatgaaaa tattttccct gattatttt ttcttgatat ctttactgaa       300
aataaagaac aaaaaaatga agaagtacca atgaaataga agtagtaaat gatggagaag     360
aagtaaaaac agaatatgta tctgaaaaaa atgaggaagt agaaaataaa tcggaaactg     420
aaataggtga agaattaact gaaaaagtag atgaaaaagt acctgaagaa gtagctgaag     480
aattagttga aaaagtagat gaagaagtag ctgaagaatt agttgaaaaa gtagatgaaa     540
aagtagctga agaagtgatc aaaaagtaga tgaagaagta actgaagaat taattgaaaa     600
agtagatgaa gaagtaactg aagaattaat tgaaaaagta gatgaagaag ttgctgaaga     660
attaattgaa aaagtagatg aagaagttgc tgaagaatta attgaaaagg tagctgatga     720
attaattgaa aaagtagatg aagaagttgc tgaagaatta attgaaaagg tagctgatga     780
attagttgaa aaagtagctg aagaattagt tgaaaaagta gatgaagaag tagctgaaga     840
attagttgaa aaagtagatg aaaaagtagc tgaagaagta gatcaaaaag tagatgaaga     900
agtaactgaa gaattaattg aaaaagtaga tgaagaagta actgaagaat taattgaaaa     960
agtagatgaa gaagttgctg aagaattaat tgaaaaagta gatgaagaag ttgctgaaga    1020
attaattgaa aaggtagctg atgaattagt tgaaaaagta gctgaagaat tagttgaaaa    1080
agtagatgaa caagtagctg aagaattagt tgaaaaagta gatgaacaag tagctgaaga    1140
attagttgaa aaagtagatg aacaagtagt tgaagaagta gctgaagaag tagctgaaga    1200
agtagttgaa gaaggtgaaa aagtacctga agaagtagct gaagaagtag ctgaagaagt    1260
agctgaagaa gtagctgaag aagtagctga agaattagtt gaaaaagtag atgaagaagt    1320
agctgaaaaa gtagttgaag aagaaggtga aaagtacct gaagaagtag ttgaagaagt     1380
agatgaagaa gtagctgaaa agtagttga agaagaaggt gaaaaagtac ttgaagaagt     1440
aattgaagaa gtagttgaag aagtagccga agaagtagct gaaaaagtag ttgaagaaca    1500
aggtgaaaaa gtaaacaaaa atgatttaaa tgatgcatct tccgaggaaa ttaaggattc    1560
tagtgatttt aaagaatctc atgaggaatt atttaaagtt ttcctggagt taattaataa    1620
aaacgattta gttaaagaaa atttaaaaaa gattacaaac aatttaaatg aaatgcattt    1680
aagcacttta tatccataa                                                  1699
```

<210> SEQ ID NO 12
<211> LENGTH: 566
<212> TYPE: PRT
<213> ORGANISM: Plasmodium falciparum

<400> SEQUENCE: 12

```
Met Leu Asn Ile Phe Asn Ile Ile Phe Leu Leu Phe Leu Ile Asn Ile
1               5                   10                  15

Tyr Ile Cys Glu Ala Asn Gly Thr Leu Ser Glu Asn Ile Glu Ser Ala
                20                  25                  30

Glu Glu Ile Asp Ala Leu Lys Thr Asn Leu Arg Asn Gly Tyr Leu Asn
            35                  40                  45

Asn Thr Tyr Phe Asn Glu Glu Asn Asn Leu Asn Ile Glu Asn Glu
        50                  55                  60

Ile Asn Asn Thr Asn Tyr Asn Glu Val Thr Glu Glu Thr Lys Glu Glu
65                  70                  75                  80

Leu Tyr Asp Ile Asn Glu Asn Ile Phe Pro Asp Tyr Phe Phe Leu Asp
                85                  90                  95
```

```
Ile Phe Thr Glu Asn Lys Glu Gln Lys Asn Glu Glu Val Pro Met Lys
                100                 105                 110

Ile Glu Val Val Asn Asp Gly Glu Glu Val Lys Thr Glu Tyr Val Ser
            115                 120                 125

Glu Lys Asn Glu Glu Val Glu Asn Lys Ser Glu Thr Glu Ile Gly Glu
        130                 135                 140

Glu Leu Thr Glu Lys Val Asp Glu Lys Val Pro Glu Glu Val Ala Glu
145                 150                 155                 160

Glu Leu Val Glu Lys Val Asp Glu Glu Val Ala Glu Glu Leu Val Glu
                165                 170                 175

Lys Val Asp Glu Lys Val Ala Glu Glu Val Asp Gln Lys Val Asp Glu
            180                 185                 190

Glu Val Thr Glu Glu Leu Ile Glu Lys Val Asp Glu Glu Val Thr Glu
        195                 200                 205

Glu Leu Ile Glu Lys Val Asp Glu Glu Val Ala Glu Glu Leu Ile Glu
    210                 215                 220

Lys Val Asp Glu Glu Val Ala Glu Glu Leu Ile Glu Lys Val Ala Asp
225                 230                 235                 240

Glu Leu Ile Glu Lys Val Asp Glu Glu Val Ala Glu Glu Leu Ile Glu
                245                 250                 255

Lys Val Ala Asp Glu Leu Val Glu Lys Val Ala Glu Glu Leu Val Glu
            260                 265                 270

Lys Val Asp Glu Glu Val Ala Glu Glu Leu Val Glu Lys Val Asp Glu
        275                 280                 285

Lys Val Ala Glu Glu Val Asp Gln Lys Val Asp Glu Glu Val Thr Glu
    290                 295                 300

Glu Leu Ile Glu Lys Val Asp Glu Glu Val Thr Glu Glu Leu Ile Glu
305                 310                 315                 320

Lys Val Asp Glu Glu Val Ala Glu Glu Leu Ile Glu Lys Val Asp Glu
                325                 330                 335

Glu Val Ala Glu Glu Leu Ile Glu Lys Val Ala Asp Glu Leu Val Glu
            340                 345                 350

Lys Val Ala Glu Glu Leu Val Glu Lys Val Asp Glu Gln Val Ala Glu
        355                 360                 365

Glu Leu Val Glu Lys Val Asp Glu Gln Val Ala Glu Glu Leu Val Glu
    370                 375                 380

Lys Val Asp Glu Gln Val Val Glu Glu Val Ala Glu Glu Val Ala Glu
385                 390                 395                 400

Glu Val Val Glu Glu Gly Glu Lys Val Pro Glu Glu Val Ala Glu Glu
                405                 410                 415

Val Ala Glu Glu Val Ala Glu Glu Val Ala Glu Glu Val Ala Glu Glu
            420                 425                 430

Leu Val Glu Lys Val Asp Glu Glu Val Ala Glu Lys Val Val Glu Glu
        435                 440                 445

Glu Gly Glu Lys Val Pro Glu Glu Val Val Glu Glu Val Asp Glu Glu
    450                 455                 460

Val Ala Glu Lys Val Val Glu Glu Gly Glu Lys Val Leu Glu Glu
465                 470                 475                 480

Val Ile Glu Glu Val Glu Glu Val Ala Glu Glu Val Ala Glu Lys
                485                 490                 495

Val Val Glu Glu Gln Gly Glu Lys Val Asn Lys Asn Asp Leu Asn Asp
            500                 505                 510

Ala Ser Ser Glu Glu Ile Lys Asp Ser Ser Asp Phe Lys Glu Ser His
```

|     |     |     |     |     |     |     |     |     |     |
| --- | --- | --- | --- | --- | --- | --- | --- | --- | --- |
|     |     |     | 515 |     |     | 520 |     |     | 525 |

Glu Glu Leu Phe Lys Val Phe Leu Glu Leu Ile Asn Lys Asn Asp Leu
            530                 535                 540

Val Lys Glu Asn Leu Lys Lys Ile Thr Asn Asn Leu Asn Glu Met His
545                 550                 555                 560

Leu Ser Thr Leu Tyr Pro
            565

<210> SEQ ID NO 13
<211> LENGTH: 2139
<212> TYPE: DNA
<213> ORGANISM: Plasmodium falciparum

<400> SEQUENCE: 13

```
atgaaatata tattaagtat tagtcttttt ttaattcttt taaatttata taaatgtgct        60
agtatatcat gtgaaataga ttacacccct agtaccaata ttactagcaa tttaaattct       120
aatttaagaa gctgttcttc taatcttgtt ctttcttcaa atatagattc tactaaatta       180
gaaggaacat atggtgaaaa tttaaacgac agtgtatctt tgacgaataa tattaatgat       240
catacaacta acgaatcaaa tatatcaaat gtatcaaata tatcaaatga atcaaatata       300
tcaaatgaat caagtataac taaccagtca aatttatcta gcgaaacaaa tatatctagc       360
gaaacaaata tatctaacga atcaagtgta ccaaatgaaa gcagtgtcaa tgaggtacct       420
caacttgaag tacctaaaga tgcagtagaa atcacacag aatccaaaga tgttttattg       480
aatgaaaagg aaaattttgc aaatggagtg gaaacacatg ttgatctagg atcccaagaa       540
caatattttg atcttccta tgatatgaat atggacacag aaggaggaat aaaaaagttc       600
aaaaatgtgt tcagtctta ttttaatcaa tccaaaggaa atagtggtac tgaaggtgat       660
ggatcaagtg tatttggatc catatttggt agcttattaa cccctataga ttcattgtta       720
gaaaaattta taggatctaa caatacaaat tcggattcta atgtgaagaa cacttctatg       780
ggaaatggac aaaataaata cgacaataat atatacttag atgaagaaga tgctttgagt       840
gatgcagaac attataatga tggtagtata agtttaggcg aagaagatga gttgagtgat       900
gcagaacatt ataatgatgg aagtataagt ttagatgaag aagatgagtt gagtgatgca       960
gaacattata tgatggagg tatatgttta ggtgaagaag atgagttaag tgatgcagaa      1020
cattataatg atggaggtat aagtttagat gaagaagatg tgttgagtga tgcagaacat      1080
tataatgatg gagatataag tttagatgaa gatgagttaa gtgatacaga aaattattat      1140
gatggaggta agtttaga cgaatcagat gatttgagtg accccgaaag taaaacaaaa      1200
gaagataact accatttata ttattgggat gatttctatc atgaatataa accaacttat      1260
ttaaattatc atatgcatta tacactttat gaaccaaaca atttttatga tactactaat      1320
gaagaaacac acaatttta taatactact aatgaagaat cacacaattt ttacaaccct      1380
actcatgaag aatcacacaa ttttacaac cctactcatg aagaatcaca caatttttac      1440
aaccctactc atgaagaatc acacaatttt tacaaccta ctcatgaaga atcacacaat      1500
ttttacaacc ctactcatga agaatcacac aattttaca ccctactcat gaagaatca      1560
cacaatttt acaaccctac tcatgaagaa tcacacaatt tttacaaccc tactcatgaa      1620
gaatcacaca attttacaa ccctactcat gaagaatcac acaatttta caaccctact      1680
catgaagaat cacacaattt ttacaaccct actcatgaag aatcacacaa ttttacacc      1740
cctactcatg aagaatcaca caatttttac aaccctactc atgaagaatc acacaatttt      1800
tacaaccta ctcatgaaga atcacacaat ttttacaacc ctactcatga agaatcacac      1860
```

-continued

```
aattttaca acccactca tgaagaatca cacaatttt acaaccctac tcatgaagaa    1920
tcacacaatt tttacacccc tactcatgat gaatttaatg ttcctttaaa ttataaccat    1980
gactacgatt acaattactt tgaaaatgat aattataata ttcaaaatgt aaagacaat     2040 ttggtaaaaa aagttaatga tttcatggaa tcagataatt tattagttaa tacctttaaa    2100
ggtatagctg ggggtgttac tagttttttc ggatattaa                           2139
```

<210> SEQ ID NO 14
<211> LENGTH: 712
<212> TYPE: PRT
<213> ORGANISM: Plasmodium falciparum

<400> SEQUENCE: 14

```
Met Lys Tyr Ile Leu Ser Ile Ser Leu Phe Leu Ile Leu Leu Asn Leu
1               5                   10                  15

Tyr Lys Cys Ala Ser Ile Ser Cys Glu Ile Asp Tyr Thr Pro Ser Thr
            20                  25                  30

Asn Ile Thr Ser Asn Leu Asn Ser Asn Leu Arg Ser Cys Ser Ser Asn
        35                  40                  45

Leu Val Leu Ser Ser Asn Ile Asp Ser Thr Lys Leu Glu Gly Thr Tyr
    50                  55                  60

Gly Glu Asn Leu Asn Asp Ser Val Ser Leu Thr Asn Asn Ile Asn Asp
65                  70                  75                  80

His Thr Thr Asn Glu Ser Asn Ile Ser Asn Val Ser Asn Ile Ser Asn
                85                  90                  95

Glu Ser Asn Ile Ser Asn Glu Ser Ser Ile Thr Asn Gln Ser Asn Leu
            100                 105                 110

Ser Ser Glu Thr Asn Ile Ser Ser Glu Thr Asn Ile Ser Asn Glu Ser
        115                 120                 125

Ser Val Pro Asn Glu Ser Ser Val Asn Glu Val Pro Gln Leu Glu Val
    130                 135                 140

Pro Lys Asp Ala Val Glu Asn His Thr Glu Ser Lys Asp Val Leu Leu
145                 150                 155                 160

Asn Glu Lys Glu Asn Phe Ala Asn Gly Val Glu Thr His Val Asp Leu
                165                 170                 175

Gly Ser Gln Glu Gln Tyr Phe Gly Ser Ser Tyr Asp Met Asn Met Asp
            180                 185                 190

Thr Glu Gly Gly Ile Lys Lys Phe Lys Asn Val Phe Gln Ser Tyr Phe
        195                 200                 205

Asn Gln Ser Lys Gly Asn Ser Gly Thr Glu Gly Asp Gly Ser Ser Val
    210                 215                 220

Phe Gly Ser Ile Phe Gly Ser Leu Leu Thr Pro Ile Asp Ser Leu Leu
225                 230                 235                 240

Glu Lys Phe Ile Gly Ser Asn Asn Thr Asn Ser Asp Ser Asn Val Lys
                245                 250                 255

Asn Thr Ser Met Gly Asn Gly Gln Asn Lys Tyr Asp Asn Asn Ile Tyr
            260                 265                 270

Leu Asp Glu Glu Asp Ala Leu Ser Asp Ala Glu His Tyr Asn Asp Gly
        275                 280                 285

Ser Ile Ser Leu Gly Glu Glu Asp Glu Leu Ser Asp Ala Glu His Tyr
    290                 295                 300

Asn Asp Gly Ser Ile Ser Leu Asp Glu Glu Asp Glu Leu Ser Asp Ala
305                 310                 315                 320

Glu His Tyr Asn Asp Gly Gly Ile Cys Leu Gly Glu Glu Asp Glu Leu
```

```
                    325                 330                 335
Ser Asp Ala Glu His Tyr Asn Asp Gly Gly Ile Ser Leu Asp Glu Glu
                340                 345                 350

Asp Val Leu Ser Asp Ala Glu His Tyr Asn Asp Gly Asp Ile Ser Leu
            355                 360                 365

Asp Glu Asp Glu Leu Ser Asp Thr Glu Asn Tyr Tyr Asp Gly Gly Ile
        370                 375                 380

Ser Leu Asp Glu Ser Asp Asp Leu Ser Asp Pro Glu Ser Lys Thr Lys
385                 390                 395                 400

Glu Asp Asn Tyr His Leu Tyr Tyr Trp Asp Asp Phe Tyr His Glu Tyr
                405                 410                 415

Lys Pro Thr Tyr Leu Asn Tyr His Met His Tyr Thr Leu Tyr Glu Pro
            420                 425                 430

Asn Asn Phe Tyr Asp Thr Thr Asn Glu Glu Thr His Asn Phe Tyr Asn
        435                 440                 445

Thr Thr Asn Glu Glu Ser His Asn Phe Tyr Asn Pro Thr His Glu Glu
    450                 455                 460

Ser His Asn Phe Tyr Asn Pro Thr His Glu Glu Ser His Asn Phe Tyr
465                 470                 475                 480

Asn Pro Thr His Glu Glu Ser His Asn Phe Tyr Asn Pro Thr His Glu
                485                 490                 495

Glu Ser His Asn Phe Tyr Asn Pro Thr His Glu Glu Ser His Asn Phe
            500                 505                 510

Tyr Asn Pro Thr His Glu Glu Ser His Asn Phe Tyr Asn Pro Thr His
        515                 520                 525

Glu Glu Ser His Asn Phe Tyr Asn Pro Thr His Glu Glu Ser His Asn
    530                 535                 540

Phe Tyr Asn Pro Thr His Glu Glu Ser His Asn Phe Tyr Asn Pro Thr
545                 550                 555                 560

His Glu Glu Ser His Asn Phe Tyr Asn Pro Thr His Glu Glu Ser His
                565                 570                 575

Asn Phe Tyr Thr Pro Thr His Glu Glu Ser His Asn Phe Tyr Asn Pro
            580                 585                 590

Thr His Glu Glu Ser His Asn Phe Tyr Asn Pro Thr His Glu Glu Ser
        595                 600                 605

His Asn Phe Tyr Asn Pro Thr His Glu Glu Ser His Asn Phe Tyr Asn
    610                 615                 620

Pro Thr His Glu Glu Ser His Asn Phe Tyr Asn Pro Thr His Glu Glu
625                 630                 635                 640

Ser His Asn Phe Tyr Thr Pro Thr His Asp Glu Phe Asn Val Pro Leu
                645                 650                 655

Asn Tyr Asn His Asp Tyr Asp Tyr Asn Tyr Phe Glu Asn Asp Asn Tyr
            660                 665                 670

Asn Ile Gln Asn Val Lys Asp Asn Leu Val Lys Lys Val Asn Asp Phe
        675                 680                 685

Met Glu Ser Asp Asn Leu Leu Val Asn Thr Phe Lys Gly Ile Ala Gly
    690                 695                 700

Gly Val Thr Ser Phe Phe Gly Tyr
705                 710

<210> SEQ ID NO 15
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 15
gaaggtaatt aaaacattgt c                                              21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gacacctcgt cgttgtaggg ag                                             22

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cggaattcca atcaagatat aatagatca                                      29

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atttgcggcc gccggtttta cccttataat g                                   31

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Lys Pro His Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Lys Pro Leu Lys Lys Pro His Pro
1               5

<210> SEQ ID NO 21
<211> LENGTH: 1260
<212> TYPE: DNA
<213> ORGANISM: Plasmodium falciparum
```

<400> SEQUENCE: 21

```
atgtggtttt gtaataaatt taatgataat acaactaaag ggttactgga ttctaataat        60
gtacaatcaa atattgtac  catatattct tttgatgatg aagaaaataa tacgaaaaga       120
aaaaatcagt tcgcatcttt tagtaaatta tgtttaaagt tatgtattct tggaattatt       180
gtaatagtgg tatgtcaaaa aaaaaaaaa  aaaaaaaaa  atttaaaata aaaataaaaa       240
ataagaaaaa aaatagtgtg catttttat  tccctacttg aatcatatat atttattcta       300
gatataaaat actaatatgt tattatatat atatatatat ttttttttg  tgtatagaac       360
gtgtgttgta gttttgaatc aaatgaaata tccaaggtta atttaataaa gaaggaatat       420
tccagaatat taagtgaaac cgaggcatta gaaaatttga agaggaaag  taaaaataga       480
aaagatgatg aagaagaagt aagtttattt gatggttctg atgatatggg tcgtacttac       540
gataatgata catggtctgt atttaatgaa gaatgtggta aaagaaaacc caagaaaaag       600
ccctagaaaa aacctcatcc tttaaaaaat aatttcgaat cattcagtta tcaatcaaga       660
tataatagat caagtatagg tgatctgatt caagttataa aatccacatt tggaggtgaa       720
gatgaacatt tatttcaaac ttgtccagat attttcgatg agttagtaaa acgttctaca       780
tgggaacgtt tggaattaga tttgtatgaa actgaaattt ctgattattt aactgtaaca       840
tatgatcttt cattaaatga aaaaattttg acattgagta gattaagtaa cgaagaagat       900
ttatacaatt tgtggtcaga aataatgaga aatgaagaaa ggaaatttag ctttctaaga       960
tatcatctat ataactacta ttattccacta aaaaatagaa gcagagtaag tcgtgaatat     1020
tcagaaaaaa tatggaatga atgtgaagaa acccttaaaa gtttacatga aagtcatgaa      1080
agttcaatct ttgatttatt ccataaatgg attaatggaa gtacatgaa  gctttcggaa      1140
tttaaagttc ttgtatctgc aggtagatat tcatggagaa atttacttaa aactggaaaa      1200
cgtgaatgta aaaatttat  gattaaacat tataagggta aaaccgcttt aagaatttaa      1260
```

<210> SEQ ID NO 22
<211> LENGTH: 1260
<212> TYPE: DNA
<213> ORGANISM: Plasmodium falciparum

<400> SEQUENCE: 22

```
atgtggtttt gtaataaatt taatgataat acaactaaag ggttactgga ttctaataat        60
gtacaatcaa atattgtac  catatattct tttgatgatg aagaaaataa tacgaaaaga       120
aaaaatcagt tcgcatcttt tagtaaatta tgtttaaagt tatgtattct tggaattatt       180
gtaatagtgg tatgtcaaaa aaaaaaaaa  aaaaaaaaa  atttaaaata aaaataaaaa       240
ataagaaaaa aaatagtgtg catttttat  tccctacttg aatcatatat atttattcta       300
gatataaaat actaatatgt tattatatat atatatatat ttttttttg  tgtatagaac       360
gtgtgttgta gttttgaatc aaatgaaata tccaaggtta atttaataaa gaaggaatat       420
tccagaatat taagtgaaac cgaggcatta gaaaatttga agaggaaag  taaaaataga       480
aaagatgatg aagaagaagt aagtttattt gatggttctg atgatatggg tcgtacttac       540
gataatgata catggtctgt atttaatgaa gaatgtggta aaagaaaacc caagaaaaag       600
cccttgaaaa aacctcatcc tttaaaaaat aatttcgaat cattcagtta tcaatcaaga       660
tataatagat caagtatagg tgatctgatt caagttataa aatccacatt tggaggtgaa       720
gatgaacatt tatttcaaac ttgtccagat attttcgatg agttagtaaa acgttctaca       780
tgggaacgtt tggaattaga tttgtatgaa actgaaattt ctgattattt aactgtaaca       840
```

| | |
|---|---|
| tatgatcttt cattaaatga aaaaattttg acattgagta gattaagtaa cgaagaagat | 900 |
| ttatacaatt tgtggtcaga aataatgaga aatgaagaaa ggaaatttag ctttctaaga | 960 |
| tatcatctat ataactacta ttattcacta aaaatagaa gcagagtaag tcgtgaatat | 1020 |
| tcagaaaaaa tatggaatga atgtgaagaa acccttaaaa gtttacatga aagtcatgaa | 1080 |
| agttcaatct tgatttatt ccataaatgg attaatggaa gtatacatga gctttcggaa | 1140 |
| tttaaagttc ttgtatctgc aggtagatat tcatggagaa atttacttaa aactggagaa | 1200 |
| cgtgaatgta aaaatttat gattaaacat tataagggta aaaccgcttt aagaatttaa | 1260 |

<210> SEQ ID NO 23
<211> LENGTH: 1092
<212> TYPE: DNA
<213> ORGANISM: Plasmodium falciparum

<400> SEQUENCE: 23

| | |
|---|---|
| atgtggtttt gtaataaatt taatgataat acaactaaag ggttactgga ttctaataat | 60 |
| gtacaatcaa atattgtac catatattct tttgatgatg aagaaaataa tacgaaaaga | 120 |
| aaaaatcagt tcgcatcttt tagtaaatta tgtttaaagt tatgtattct tggaattatt | 180 |
| gtaatagtga acgtgtgttg tagttttgaa tcaaatgaaa tatccaaggt taatttaata | 240 |
| aagaaggaat attccagaat attaagtgaa accgaggcat tagaaaattt gaaagaggaa | 300 |
| agtaaaaata gaaaagatga tgaagaagaa gtaagtttat ttgatggttc tgatgatatg | 360 |
| ggtcgtactt acgataatga tacatggtct gtatttaatg aagaatgtgg taaaagaaaa | 420 |
| cccaagaaaa agccctagaa aaaacctcat cctttaaaaa ataatttcga atcattcagt | 480 |
| tatcaatcaa gatataatag atcaagtata ggtgatctga ttcaagttat aaaatccaca | 540 |
| tttggaggtg aagatgaaca tttatttcaa acttgtccag atattttcga tgagttagta | 600 |
| aaacgttcta catgggaacg tttggaatta gatttgtatg aaactgaaat ttctgattat | 660 |
| ttaactgtaa catatgatct ttcattaaat gaaaaaattt tgacattgag tagattaagt | 720 |
| aacgaagaag attttatacaa tttgtggtca gaaataatga gaaatgaaga aggaaatttt | 780 |
| agctttctaa gatatcatct atataactac tattattcac taaaaaatag aagcagagta | 840 |
| agtcgtgaat attcagaaaa aatatggaat gaatgtgaag aaacccttaa agtttacat | 900 |
| gaaagtcatg aaagttcaat ctttgattta ttccataaat ggattaatgg aagtatacat | 960 |
| gagctttcgg aatttaaagt tcttgtatct gcaggtagat attcatggag aaatttactt | 1020 |
| aaaactggag aacgtgaatg taaaaaattt atgattaaac attataaggg taaaaccgct | 1080 |
| ttaagaattt aa | 1092 |

<210> SEQ ID NO 24
<211> LENGTH: 1092
<212> TYPE: DNA
<213> ORGANISM: Plasmodium falciparum

<400> SEQUENCE: 24

| | |
|---|---|
| atgtggtttt gtaataaatt taatgataat acaactaaag ggttactgga ttctaataat | 60 |
| gtacaatcaa atattgtac catatattct tttgatgatg aagaaaataa tacgaaaaga | 120 |
| aaaaatcagt tcgcatcttt tagtaaatta tgtttaaagt tatgtattct tggaattatt | 180 |
| gtaatagtga acgtgtgttg tagttttgaa tcaaatgaaa tatccaaggt taatttaata | 240 |
| aagaaggaat attccagaat attaagtgaa accgaggcat tagaaaattt gaaagaggaa | 300 |
| agtaaaaata gaaaagatga tgaagaagaa gtaagtttat ttgatggttc tgatgatatg | 360 |

```
ggtcgtactt acgataatga tacatggtct gtatttaatg aagaatgtgg taaaagaaaa      420
cccaagaaaa agcccttgaa aaaacctcat cctttaaaaa ataatttcga atcattcagt      480
tatcaatcaa gatataatag atcaagtata ggtgatctga ttcaagttat aaaatccaca      540
tttggaggtg aagatgaaca tttatttcaa acttgtccag atattttcga tgagttagta      600
aaacgttcta catgggaacg tttggaatta gatttgtatg aaactgaaat ttctgattat      660
ttaactgtaa catatgatct ttcattaaat gaaaaaattt tgacattgag tagattaagt      720
aacgaagaag atttatacaa tttgtggtca gaaataatga gaaatgaaga aggaaatttt      780
agctttctaa gatcatctct atataactac tattattcac taaaaaatag aagcagagta      840
agtcgtgaat attcagaaaa aatatggaat gaatgtgaag aaacccttaa aagtttacat      900
gaaagtcatg aaagttcaat ctttgattta ttccataaat ggattaatgg aagtatacat      960
gagctttcgg aatttaaagt tcttgtatct gcaggtagat attcatggag aaatttactt     1020
aaaactggag aacgtgaatg taaaaaattt atgattaaac attataaggg taaaaccgct     1080
ttaagaattt aa                                                          1092

<210> SEQ ID NO 25
<211> LENGTH: 1092
<212> TYPE: DNA
<213> ORGANISM: Plasmodium falciparum

<400> SEQUENCE: 25
atgtggtttt gtaataaatt taatgataat acaactaaag ggttactgga ttctaataat       60
gtacaatcaa aatattgtac catatattct tttgatgatg aagaaaataa tacgaaaaga      120
aaaaatcagt tcgcatcttt tagtaaatta tgtttaaagt tatgtattct tggaattatt      180
gtaatagtga acgtgtgttg tagttttgaa tcaaatgaaa tatccaaggt taatttaata      240
aagaaggaat attccagaat attaagtgaa accgaggcat tagaaaattt gaaagaggaa      300
agtaaaaata gaaaagatga tgaagaagaa gtaagtttat ttgatggttc tgatgatatg      360
ggtcgtactt acgataatga tacatggtct atatttaatg aagaatgtgg taaaagaaaa      420
cccaagaaaa agcccttgaa aaaacctcat cctttaaaaa ataatttcga atcattcagt      480
tatcaatcaa gatataatag atcaagtata ggtgatctga ttcaagttat aaaatccaca      540
tttggaggtg aagatgaaca tttatttcaa acttgtccag atattttcga tgagttagta      600
aaacgttcta catgggaacg tttggaatta gatttgtatg aaactgaaat ttctgattat      660
ttaactgtaa catatgatct ttcattaaat gaaaaaattt tgacattgag tagattaagt      720
aacgaagaag atttatacaa tttgtggtca gaaataatga gaaatgaaga aggaaatttt      780
agctttctaa gatcatctct atataactac tattattcac taaaaaatag aagcagagta      840
agtcgtgaat attcagaaaa aatatggaat gaatgtgaag aaacccttaa aagtttacat      900
gaaagtcatg aaagttcaat ctttgattta ttccataaat ggattaatgg aagtatacat      960
gagctttcgg aatttaaagt tcttgtatct gcaggtagat attcatggag aaatttactt     1020
aaaactggag aacgtgaatg taaaaaattt atgattaaac attataaggg taaaaccgct     1080
ttaagaattt aa                                                          1092

<210> SEQ ID NO 26
<211> LENGTH: 999
<212> TYPE: DNA
<213> ORGANISM: Plasmodium falciparum

<400> SEQUENCE: 26
```

```
atgtggtttt gtaataaatt taatgataat acaactaaag ggttactgga ttctaataat    60
gtacaatcaa aatattgtac catatattct tttgatgatg aagaaaataa tacgaaaaga   120
aaaaatcagt tcgcatcttt tagtaaatta tgtttaaagt tatgtattct tggaattatt   180
gtaatagtga acgtgtgttg tagttttgaa tcaaatgaaa tatccaaggt taatttaata   240
aagaaggaat attccagaat attaagtgaa accgaggcat tagaaaattt gaaagaggaa   300
agtaaaaata gaaaagatga tgaagaagaa gtaagtttat ttgatggttc tgatgatatg   360
ggtcgtactt acgataatga tacatgttat caatcaagat ataatagatc aagtataggt   420
gatctgattc aagttataaa atccacattt ggaggtgaag atgaacattt atttcaaact   480
tgtccagata ttttcgatga gttagtaaaa cgttctacat gggaacgttt ggaattagat   540
ttgtatgaaa ctgaaatttc tgattattta actgtaacat atgatctttc attaaatgaa   600
aaaattttga cattgagtag attaagtaac gaagaagatt tatacaattt gtggtcagaa   660
ataatgagaa atgaagaaag gaaatttagc tttctaagat atcatctata taactactat   720
tattcactaa aaaatagaag cagagtaagt cgtgaatatt cagaaaaaat atggaatgaa   780
tgtgaagaaa cccttaaaag tttacatgaa agtcatgaaa gttcaatctt tgatttattc   840
cataaatgga ttaatggaag tatacatgag ctttcggaat ttaaagttct tgtatctgca   900
ggtagatatt catggagaaa tttacttaaa actggagaac gtgaatgtaa aaaatttatg   960
attaaacatt ataagggtaa aaccgcttta agaatttaa                          999
```